US010251902B2

(12) United States Patent
Ryu et al.

(10) Patent No.: US 10,251,902 B2
(45) Date of Patent: Apr. 9, 2019

(54) PHARMACEUTICAL COMPOSITION FOR TREATING OR PREVENTING NEUROPSYCHIATRIC DISEASE, CONTAINING FLAVONE-6-C-GLUCOSE DERIVATIVES AS ACTIVE INGREDIENTS

(71) Applicant: DAE HWA PHARMA. CO., LTD., Gangwon-do (KR)

(72) Inventors: Jong Hoon Ryu, Seoul (KR); Jae Hoon Cheong, Gyeonggi-do (KR); Chan Young Shin, Seoul (KR); Dae Sik Jang, Seoul (KR); Hyung Eun Lee, Seoul (KR); Hyun Ji Kim, Seoul (KR); Byeol Ryu, Seoul (KR); In Ho Jung, Gyeonggi-do (KR); Yeong Woo Jo, Seoul (KR)

(73) Assignee: DAE HWA PHARMA CO., LTD., Gangwon-do (KR)

(*) Notice: Subject to any disclaimer, the term of this patent is extended or adjusted under 35 U.S.C. 154(b) by 87 days.

(21) Appl. No.: 14/912,069

(22) PCT Filed: Aug. 14, 2014

(86) PCT No.: PCT/KR2014/007569
§ 371 (c)(1),
(2) Date: Apr. 1, 2016

(87) PCT Pub. No.: WO2015/023142
PCT Pub. Date: Feb. 19, 2015

(65) Prior Publication Data
US 2016/0206640 A1    Jul. 21, 2016

(30) Foreign Application Priority Data

Aug. 14, 2013  (KR) .................. 10-2013-0096493

(51) Int. Cl.
| | |
|---|---|
| *A61K 31/7048* | (2006.01) |
| *A61K 31/352* | (2006.01) |
| *A61K 36/51* | (2006.01) |
| *A23L 33/105* | (2016.01) |
| *A61K 36/00* | (2006.01) |

(52) U.S. Cl.
CPC ........ *A61K 31/7048* (2013.01); *A23L 33/105* (2016.08); *A61K 31/352* (2013.01); *A61K 36/51* (2013.01); *A61K 36/00* (2013.01)

(58) Field of Classification Search
None
See application file for complete search history.

(56) References Cited

U.S. PATENT DOCUMENTS

| 4,987,150 A | * | 1/1991 | Kurono ................. A61K 31/35 514/455 |
|---|---|---|---|
| 2008/0214658 A1 | | 9/2008 | Woo et al. ..................... 514/456 |
| 2011/0159122 A1 | * | 6/2011 | Frank .................. A61K 36/258 424/728 |
| 2015/0065441 A1 | | 3/2015 | Ryu et al. ....................... 514/27 |

FOREIGN PATENT DOCUMENTS

| CN | 101433561 A | 5/2009 |
|---|---|---|
| EP | 1 666 051 | 6/2006 |
| JP | 2006-124376 A | 5/2006 |
| JP | 2006-143658 A | 6/2006 |
| JP | 2007-126455 A | 5/2007 |
| JP | 2013-040121 A | 2/2013 |
| KR | 10-2003-0013382 | 2/2003 |
| KR | 10-2007-0039406 | 4/2007 |
| WO | WO 2007-137380 | 12/2007 |
| WO | WO 2008/046149 | 4/2008 |
| WO | WO2009/121155 | * 10/2009 |
| WO | WO 2009-121155 | 10/2009 |
| WO | WO 2013/081419 | 6/2013 |

OTHER PUBLICATIONS

Sena et al, Experimental Biology and Medicine, 2009, 234(8), pp. 967-975.*
Reddy et al., International Journal of Phytopharmacology, 3(1), 2012, 61-65.*
Letter/Written Disclosure of the Information Disclosure Statement for the above-referenced application, filed herewith on May 12, 2016, 2 pages.
Akhondzadeh et al., "Melissa officinalis extract in the treatment of patients with mild to moderate Alzheimer's disease: a double blind, randomised, placebo controlled trial." J Neurol Neurosurg Psychiatry 74:863-866 (2003).
Broekkamp et al., "Major tranquilizers can be distinguished from minor tranquilizers on the basis of effects on marble burying and swim-induced grooming in mice." Eur J Pharmacol., 126: 223-229 (1986).
Cummings et al., "Behavioral effects of current Alzheimer's disease treatments; a descriptive review." Alzheimers Dement 4:49-60 (2008).
Ebert et al., "Scopolamine model of dementia: electroencephalogram findings and cognitive performance." Eur J Clin Invest 28: 944-949 (1998).
Cheng et al., "Flavonoids from *Ziziphus jujuba* Mill var. *spinosa*." Tetrahedron 56:8915-8920 (2000).

(Continued)

*Primary Examiner* — Traviss C McIntosh, III
(74) *Attorney, Agent, or Firm* — Dentons US LLP; Stephanie Seidman

(57) ABSTRACT

The present invention provides a pharmaceutical composition or a food composition comprising, as active ingredients, flavone-6-C-glucose derivatives or galenical extracts containing flavone-6-C-glucose derivatives. The composition of the present invention shows a functional effect of effectively treating or preventing cognitive dysfunction disorders such as delirium, dementia or amnesia, stroke, palsy, attention disorders, anxiety disorders or sleep disorders.

13 Claims, 8 Drawing Sheets

(56) References Cited

OTHER PUBLICATIONS

Kar et al., "Interactions between beta-amyloid and central cholinergic neurons: implications for Alzheimer's disease." J Psychiatry Neurosci. 29: 427-441 (2004).
Li et al., "The glycosides from Lomatogonium rotatum." Nat Prd Res 22:198-202 (2008).
Reddy et al. "Evaluation of diuretic activity of methanolic extract of *Oxalis corniculata* L. in rats." Intl J Phytopharmacology 3:61-65 (2012).
Sarter et al., "Attenuation of scopolamine-induced impairment of spontaneous alternation behaviour by antagonist but not inverse agonist and agonist beta-carbolines." Psychopharmacology 94: 491-495 (1988).
Terry et al., "The cholinergic hypothesis of age and Alzheimer's disease-related cognitive deficits: Recent challenges and their implications for novel drug development." J Pharmacol and Exp Ther 306:821-827 (2003).
Voss et al., "Brain substrates of implicit and explicit memory: The importance of concurrently acquired neural signals of both memory types." Neuropsychologia 46: 3021-3029 (2008).
International Preliminary Report on Patentability amnd Written Opinion, dated, Feb. 16, 2016, in connection with International Patent Application No. PCT/KR2014/007569 [English translation], 10 pages.
International Search Report, dated Nov. 21, 2014, in connection with International Patent Application No. PCT/KR2014/007569 [English translation], 3 pages.
Letter/Written Disclosure of the Supplemental Information Disclosure Statement for the above-referenced application, filed herewith on Feb. 16, 2017, 3 pages.
Akhondzadeh et al., "Passiflora incarnata in the treatment of attention-deficit hyperactivity disorder in children and adolescents," Therapy 2(4):609-614 (2005).
Dhawan et al., "Suppression of alcohol-cessation-oriented hyper-anxiety by the benzoflavone moiety of Passiflora incarnata Linneaus in mice," Journal of Ethnopharmacology 81(2):239-244 (2002).
Machine-generated English language translation of JP 2013-040121 A, published Feb. 2, 2017, PatentScope, World Intellectual Property Organization, 6 pages.
Extended European Search Report, dated Jan. 18, 2017, in connection with corresponding European Patent Application No. 14836794.9, 9 pages.
Letter/Written Disclosure of the Supplemental Information Disclosure Statement for the above-referenced application, filed herewith on Mar. 7, 2016, 3 pages.
Conforti et al., "Protection against neurodegenerative diseases of Iris pseudopumila extracts and their constituents," Fitoterapia 80:62-27 (2009).
Office Action, dated Feb. 14, 2017, in connection with Japanese Patent Application No. 534534/2016 [English translation and original document in Japanese], 11 pages.
Letter/Written Disclosure of the Supplemental Information Disclosure Statement for the above-referenced application, filed herewith on Dec. 20, 2016, 2 pages.
Mizokami et al., "Flavonoids in the leaves of *Oxalis corniculata* and sequestration of the flavonoids in the wing scales of the pale grass blue butterfly, *Pseudozizeeria maha*," J. Plant Res. 121:133-136 (2008).
Mukherjee et al., "*Oxalis corniculata* (Oxalidaceae) Leaf Extract Exerts In Vitro Antimicrobial and In Vivo Anticolonizing Activities Against *Shigella dysenteriae* 1 (NT4907) and *Shigella flexneri* 2a (2457T) in Induced Diarrhea in Suckling Mice," J. Med. Food 16(9):801-809 (2013).
Reddy et al., "Effect of *Oxalis corniculata* on Cortecosterone Induced Memory Impairement in Male Albino Mice," International Journal of Pharmacy & Therapeutics, 1(1):34-39 (2010).
Letter/Written Disclosure of the Supplemental Information Disclosure Statement for the above-referenced application, filed herewith on Sep. 21, 2018, 2 pages.
Akhondzadeh et al., "Passionflower in the treatment of generalized anxiety: a pilot double-blind randomized controlled trial with oxazepam," J. Clin. Pharm. Ther. 26:363-367 (2001).
Espacenet generated English language abstract of CN 101433561 (A), published May 20, 2009, 1 page.
Espacenet generated English language abstract of JP 2007-126455 (A), published May 24, 2007, 1 page.
Lee et al., "Effects of a Korean traditional herbal supplement on symptoms of stress and mood profiles in high school girls: a randomized, double blind, placebo-controlled trial," Stress and Health 21:139-143 (2005).
Ngan, A. and R. Conduit, "A Double-blind, Placebo-controlled Investigation of the Effects of *Passiflora incarnata* (Passionflower) Herbal Tea on Subjective Sleep Quality," Phytotherapy Research 25:1153-1159 (2011).
Response, filed Aug. 2, 2017, to Extended European Search Report, dated Jan. 18, 2017, in connection with corresponding European Patent Application No. 14836794.9 [D1=Reddy et al., "Evaluation of diuretic activity of methanolic extract of *Oxalis corniculata* L. in rats," Intl J Phytopharmacology 3:61-65 (2012); D2=WO 2007/137380; D3=WO 2009/121155; D4=KR20030013382; D5=KR20070039406; D6=Reddy et al., "Effect of *Oxalis corniculata* on Corticosterone Induced Memory Impairement in Male Albino Mice," International Journal of Pharmacy & Therapeutics, 1(1):34-39 (2010); D7=JP2013040121; D8=Dhawan et al., "Suppression of alcohol-cessation-oriented hyper-anxiety by the benzoflavone moiety of Passiflora incarnata Linneaus in mice," Journal of Ethnopharmacology 81(2):239-244 (2002); D9=Akhondzadeh et al., "Passiflora incarnata in the treatment of attention-deficit hyper-activity disorder in children and adolescents," Therapy 2(4):609-614 (2005)], 20 pages.
Communication pursuant to Article 94(3) EPC (Examination Report), dated Aug. 9, 2018, in connection with European Patent Application No. 14 836 794.9 [D4=KR20030013382; D6=Reddy et al., "Effect of *Oxalis corniculata* on Corticosterone Induced Memory Impairement in Male Albino Mice," International Journal of Pharmacy & Therapeutics, 1(1):34-39 (2010)], 7 pages.
Decision of Refusal, dated Jul. 31, 2018, in connection with Japanese Patent Application No. 534534/2016 [English translation and original document in Japanese], 7 pages.
Office Action, dated Aug. 30, 2018, in connection with Chinese Patent Application No. 201480056351.2 [English translation and original document in Chinese], 21 pages.

* cited by examiner

[FIG.1]
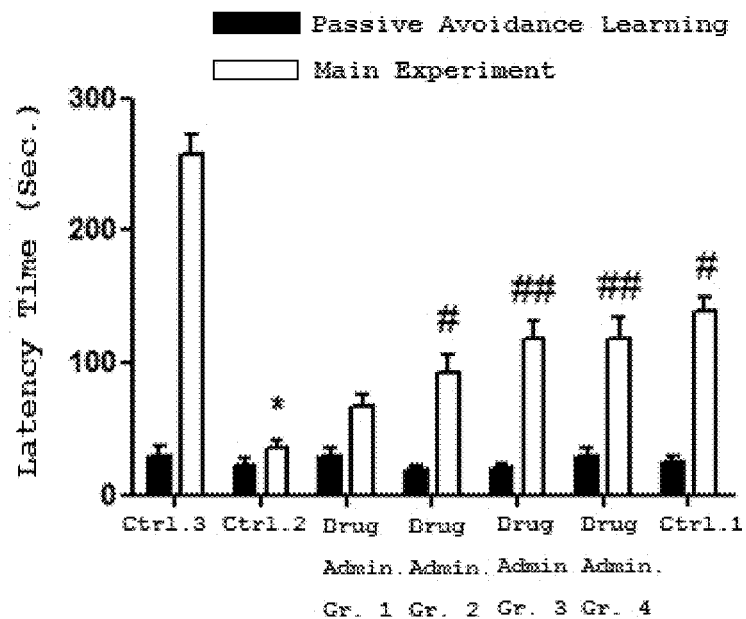
[FIG.2]
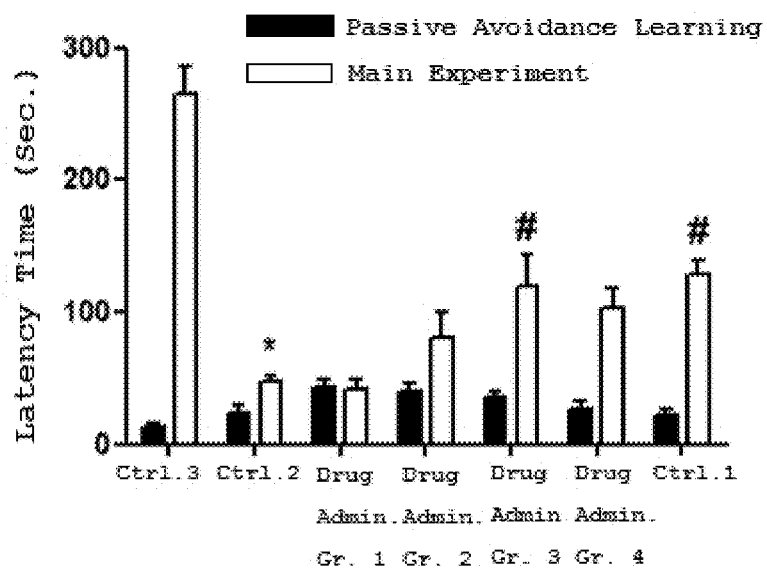

[FIG.3]
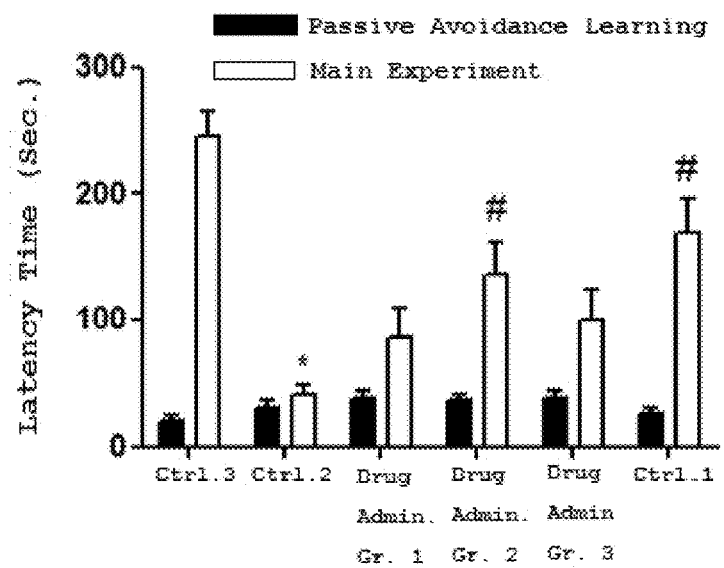
[FIG.4]
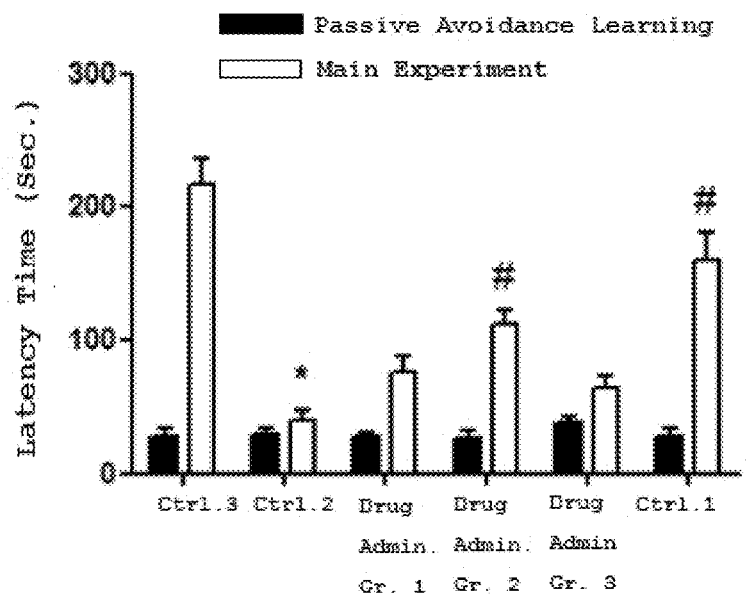

[FIG.5]
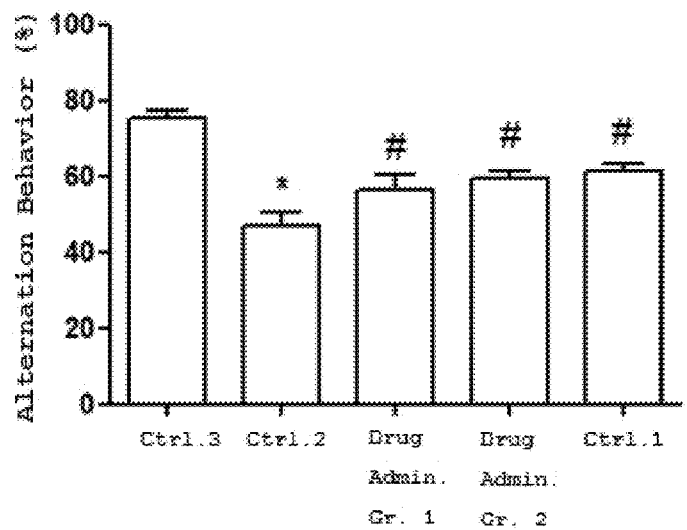
[FIG.6]
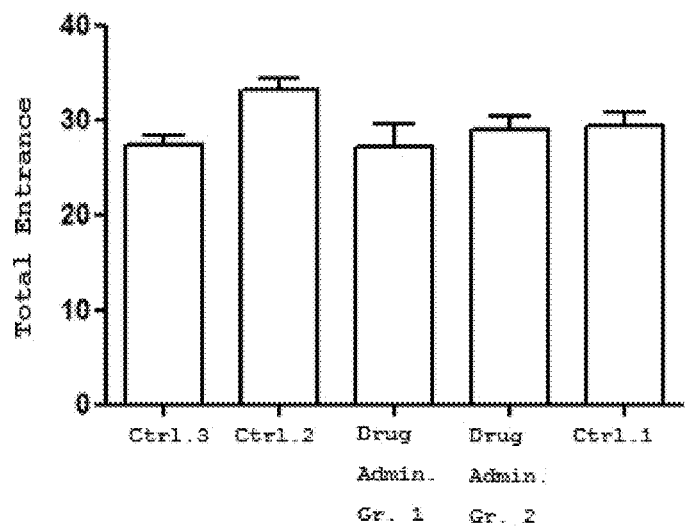

[FIG.7]
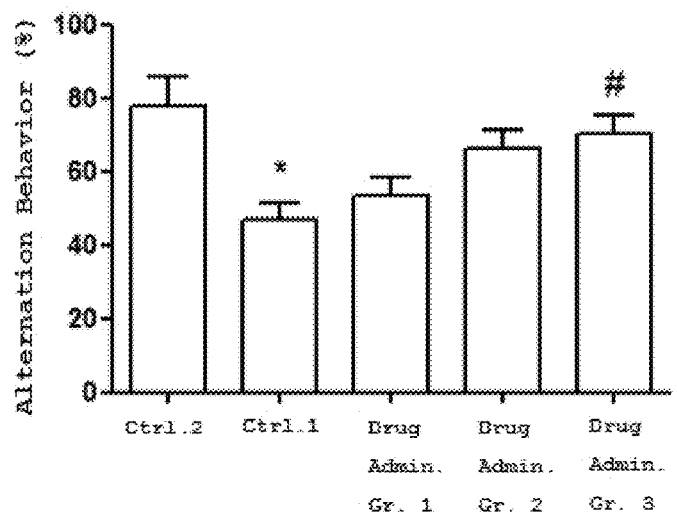
[FIG.8]
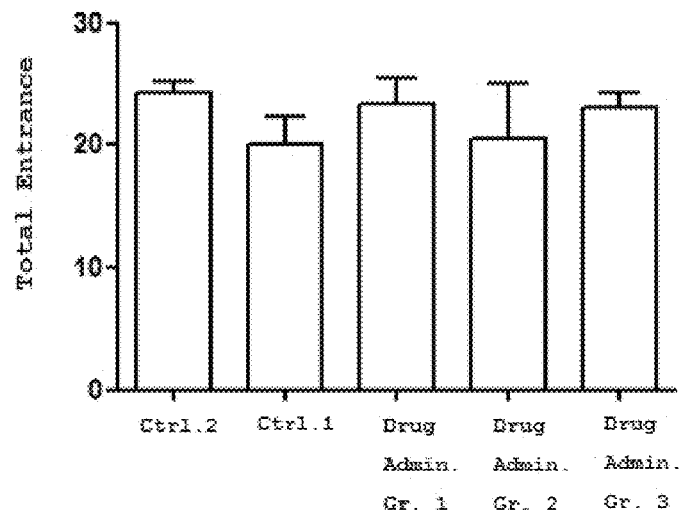

[FIG.9]
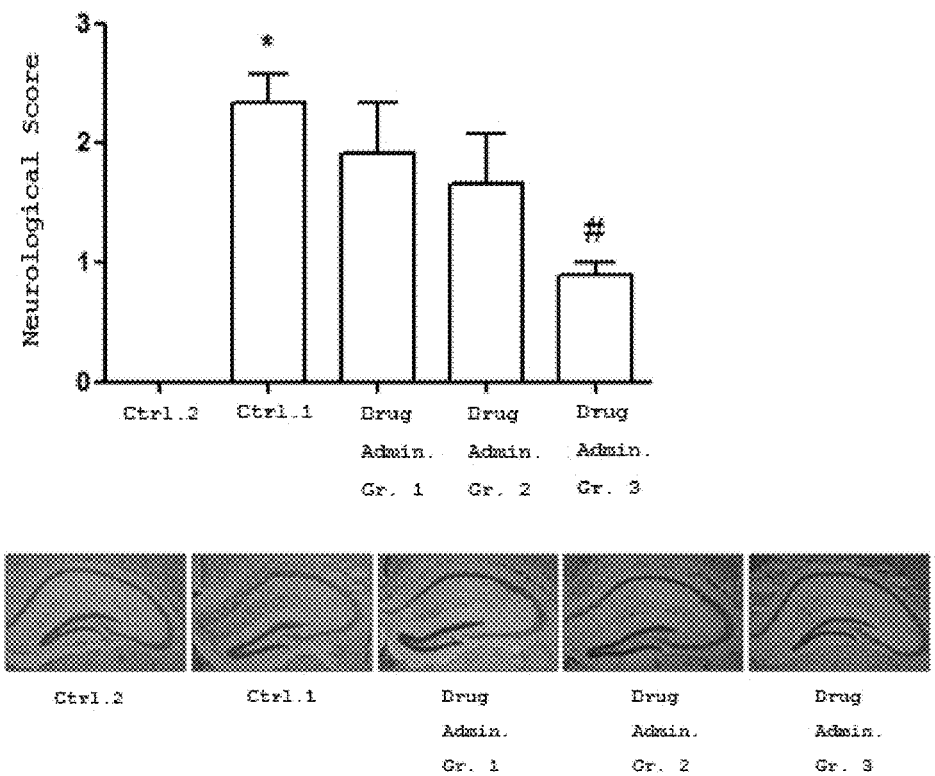
[FIG.10]
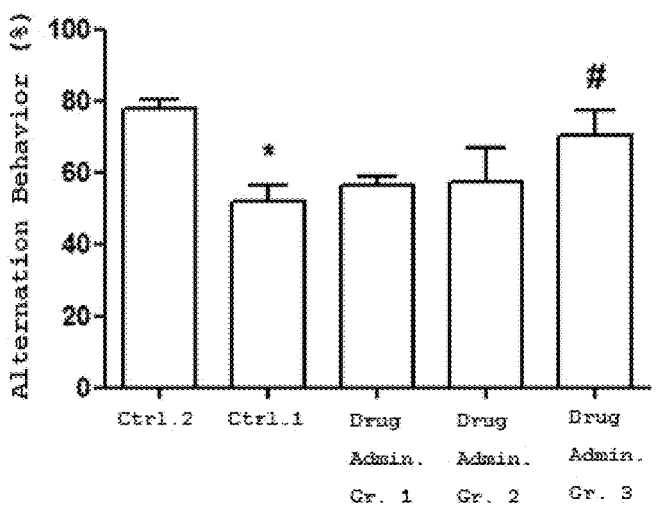

[FIG.11]
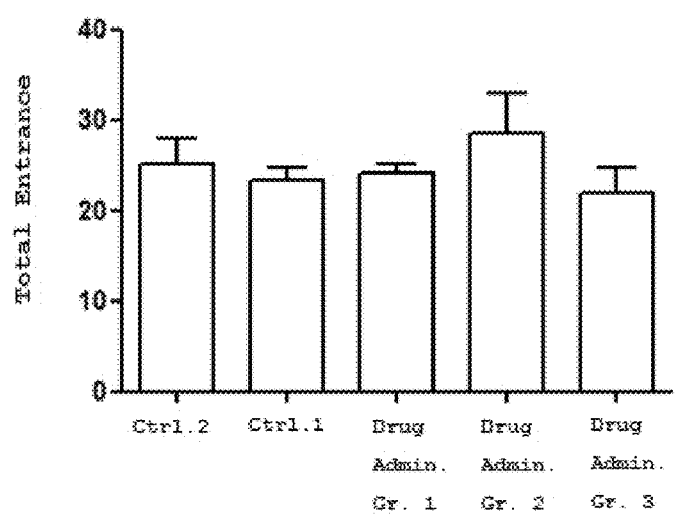

[FIG.12]
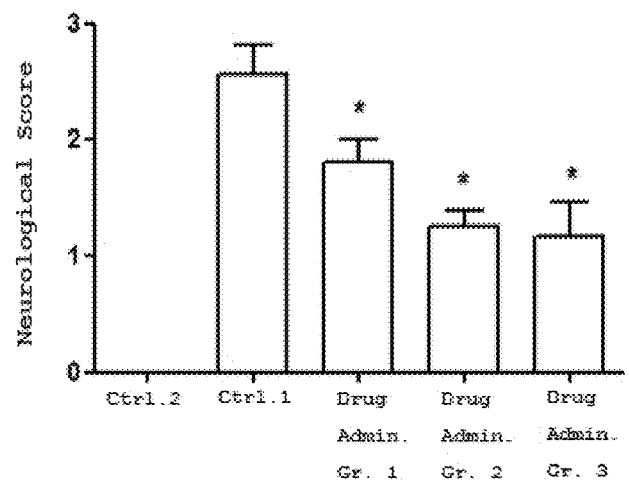
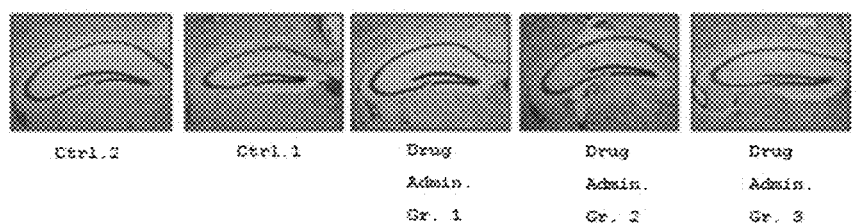
[FIG.13]
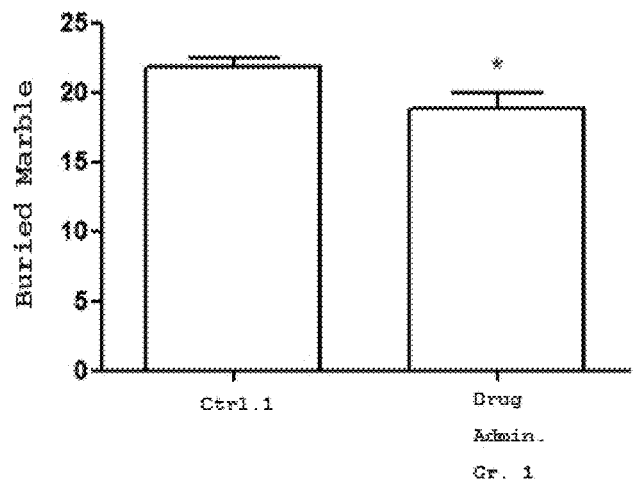

[FIG.14]
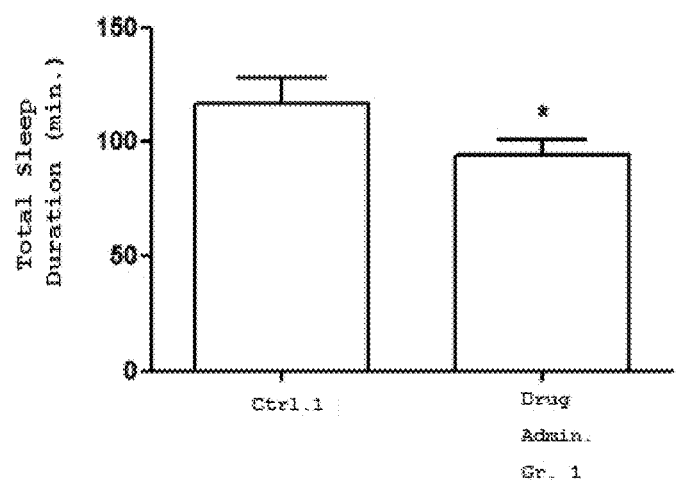

PHARMACEUTICAL COMPOSITION FOR TREATING OR PREVENTING NEUROPSYCHIATRIC DISEASE, CONTAINING FLAVONE-6-C-GLUCOSE DERIVATIVES AS ACTIVE INGREDIENTS

RELATED APPLICATIONS

This application is the U.S. National Stage of International Application. No. PCT/KR2014/007569, filed 14 Aug. 2014, which claims benefit of priority to Korean Patent Application KR 10-2013-0096493, filed 14 Aug. 2013, the specification of which is incorporated by reference herein.

TECHNICAL FIELD

The present disclosure relates to a pharmaceutical composition for preventing or treating neuropsychiatric disease, comprising flavone-6-C-β-D-glucose derivatives or herbal extracts containing the same as active ingredients.

Also, the present disclosure relates to a food composition for preventing or improving neuropsychiatric disease, comprising flavone-6-C-β-D-glucose derivatives or herbal extracts containing the same as active ingredients.

BACKGROUND

Dementia is a morbid condition in which difficulties lie in everyday life because of continuous decline of intellectual skills such as memory, language, judgment, thinking abilities and the like due to damages in brain function. Dementia, a representative disease of cognitive disorders, is a morbid phenomenon that should be distinguished from normal aging. Dementia is categorized into Alzheimer's disease, vascular dementia, alcoholic dementia, traumatic dementia and dementia due to aftereffects of Parkinson's disease depending on its causes. It is known that Alzheimer's disease accounts for 50% to 70% of diseases causing dementia, and vascular dementia is known to be the second most frequent cause of dementia. The proportion of dementia patients are rapidly increasing in South Korea and it is expected to be accelerated further. Therefore, demand for development of functional substances and food and the like for preventing and treating cognitive diseases including dementia is growing in these days.

Apropos of Alzheimer's disease, decline of acetylcholine function in the central nervous system is the most common phenomenon. Therefore, administration of acetylcholine precursors or drugs inhibiting decomposition of acetylcholine for increasing concentration of acetylcholine in brain has been used to treat Alzheimer's disease. Thus, single use of acetylcholinesterase inhibitors or combined use with previous cholinesterase inhibitors is used as a medicament for Alzheimer's disease. Representative drugs would be tacrine, donepezil, rivastigmine, galantamine and the like.

Vascular dementia due to stroke or palsy is mostly caused by damages to the brain cells due to insufficient blood supply to many areas of the brain by cerebrovascular atherosclerosis. An anticoagulant such as aspirin and warfarin and the like is being used as a platelet aggregation inhibitor, which prevents cerebrovascular diseases that could occur from thrombus for treating vascular dementia.

Drugs in use of treating Alzheimer's disease or vascular dementia merely delay the progression of disease and not that effective in direct treatment. Also, therapeutic range of these is limited to the initial stage, therefore the efforts to develop a drug for treating the root cause of dementia have been made. Reasons for onset of vascular dementia and Alzheimer's disease are different, but both eventually impairs the memory in common (Terry and Buccafusco, 2003; Kar et al., 2004; Akhondzadeh et al., 2008; Cummings et al., 2008; Voss et al., 2008).

Meanwhile, although anxiety is recognized as a normal response to adapt to the changing circumstances, but when excessive anxiety persists for more than 6 months, it can be deemed to be an anxiety disorder. Morbid anxiety can cause severe pain to the patients themselves as well as their family and surrounding people, and the reason of it is known as an abnormal nerve structure. Anxiety disorder treatment is accompanied with psychotherapy and medicine treatment, and drugs having various routes of action mechanism are used for the medicine treatment. However, use of anti-anxiety drugs should be made cautiously because of anxiolytic effect as well as side effects such as withdrawal and sedation symptoms. Accordingly, investigation on anti-anxiety drug without side effects, which is made of natural substances, has emerged as a major problem.

Hypersomnias means a lot more sleep than a normal sleep. It is a status of feeling fatigue and causing problems to attention ability due to constant awareness of lack of sleep even though there was enough sleep and no specific reason. Attention ability is important for learning or judging something, and maintaining concentration is a major factor in making quick decision and judgment that can lead to the most effective action while conducting series of work. However, maintaining concentration for a long time is very difficult because it is hindered by various external factors, and substances having awakening effect, which can extend duration of concentration, have been researched. Glucose intake and substances such as caffeine and the like, which increase mind concentration while workout, are known to be effective for short-term increase of concentration. However, glucose can increase blood sugar temporarily but has no continuity, and caffeine has relatively longer duration but has symptoms of intoxication when taking it excessively. Thus a novel drug that has no toxicity and longer duration is required.

Accordingly, the present inventors discovered a herbal extract and its active ingredients, which can effectively increase memory and learning abilities, while researching on development of effective therapeutic agents for preventing or treating cognitive disorders such as dementia and the like, and found out that the same has superior effect in concentration, anti-anxiety effect and awakening effect as well as memory when applying the same to various psychoneurological diseases. Succeedingly, the present inventors completed the present disclosure.

SUMMARY

Technical Problem

It is an object of the present disclosure to provide a pharmaceutical composition for preventing or treating cognitive disorders, stroke, palsy, attention disorders, anxiety disorders or sleep disorders comprising flavone-6-C-β-D-glucose derivatives as active ingredients.

Another object of the present disclosure is to provide a pharmaceutical composition for preventing or treating cognitive disorders, stroke, palsy, attention disorders, anxiety disorders or sleep disorders comprising an herbal extract containing the flavone-6-C-β-D-glucose derivatives as active ingredients.

Still another object of the present disclosure is to provide a food composition for preventing or improving cognitive disorders, stroke, palsy, attention disorders, anxiety disorders or sleep disorders comprising the flavone-6-C-β-D-glucose derivatives.

Still another object of the present disclosure is to provide a food composition for preventing or improving cognitive disorders, stroke, palsy, attention disorders, anxiety disorders or sleep disorders comprising the herbal extract comprising the flavone-6-C-β-D-glucose derivatives as active ingredients.

Still another object of the present disclosure is to provide a method for preventing, improving or treating cognitive disorders, stroke, palsy, attention disorders, anxiety disorders or sleep disorders by administering the pharmaceutical composition or the food composition to subjects in need of the same.

Still another object of the present disclosure is to provide a use of the pharmaceutical composition or the food composition for preparation of a therapeutic agent for preventing, improving or treating cognitive disorders, stroke, palsy, attention disorders, anxiety disorders or sleep disorders.

Solution to Problem

Pharmaceutical Composition
Composition Comprising flavone-6-C-β-D-glucose Derivatives The present disclosure provides the pharmaceutical composition for preventing or treating cognitive disorders, stroke, palsy, attention disorders, anxiety disorders or sleep disorders comprising flavone-6-C-β-D-glucose as an active ingredient.

The flavone-6-C-β-D-glucose derivative is a compound represented by Formula 1 below.

[Formula 1]

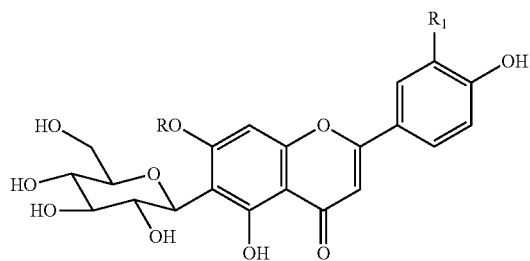

In Formula 1,
R is H or $C_1$-$C_6$ alkyl, and
$R_1$ is H or OH.
The flavone-6-C-β-D-glucose derivatives can be selected from a group consisting of swertisin, isovitexin, isoorientin, swertiajaponin stated in Table 1, and mixtures thereof. Most preferably, it can be swertisin.

TABLE 1

| Compound | R | $R_1$ |
|---|---|---|
| Swertisin | $CH_3$ | H |
| Isovitexin | H | H |
| Isoorientin | H | OH |
| Swertiajaponin | $CH_3$ | OH |

The flavone-6-C-β-D-glucose derivatives represented by Formula 1 can be yielded from various kinds of herbal drugs. For instance, swertisin, isovitexin, isoorientin or swertiajaponin can be yielded from *Swertia japonica, Swertia pseudochinensis, Enicostemma hyssopifolium, Swertia mussotii* Franch, *Enicostemma hyssopifolium, Swertia franchetiana, Gentianella austriaca* (Gentianaceae), *Machaerium hirtum* Vell. (Fabaceae), *Aleurites moluccana* L. *Willd.* (Euforbiaceae), *Zizyphus spinosa* (Rhamnaceae), *Belamcanda chinensis* (Iridaceae), *Wilbrandia ebracteata, Cayaponia tayuya* (Cucurbitaceae), *Passiflora incarnata* L. (Passifloraceae), *Commelina communis* L. (Commelinaceae), *Oxalis corniculata* (Oxalidaceae) and *Aquilegia oxysepala* Trautv. et Mey (Ranunculoideae), or mixtures thereof.

In detail, the flavone-6-C-β-D-glucose derivatives can be yielded from extracts of the herbal drugs. For instance, swertisin, which is one of the flavone-6-C-β-D-glucose derivatives represented by Formula 1, can be yielded from a whole plant of *Swertia japonica* or a whole plant of *Swertia pseudochinensis*.

An extract solvent for the herbal extracts can be water, alcohol, hexane or mixtures thereof. It is preferable for the alcohol to be $C_1$-$C_4$ lower alcohol, and more preferably to be methanol or ethanol. An extraction method can be shaking extraction, Soxhlet extraction or reflux extraction but not limited to these. It is preferable for extraction temperature to be 40-100° C., and more preferably to be 60-80° C. In addition, it is preferable for extraction duration to be 2-24 hours, and 1-5 times for the extraction time.

Also, swertisin, isovitexin, isoorientin or swertiajaponin of the flavone-6-C-β-D-glucose derivatives represented by Formula 1 can be purchased from the commercial market or yielded by organic synthesis.

The pharmaceutical composition of the present disclosure comprising the flavone-6-C-β-D-glucose derivatives as active ingredients can be used for preventing or treating cognitive disorders, stroke, palsy, attention disorders, anxiety disorders or sleep disorders.

Apropos of the present disclosure, the cognitive disorders are directed to neuropsychiatric diseases incurred from functional decline of memory, space skills, concentration, judgment, executive function, linguistic ability and the like. It can be delirium, dementia or amnesia. Also, the dementia can be caused by various causes such as Alzheimer's disease, vascular dementia, attention deficit hyperaction disorder, alcoholic dementia, traumatic dementia and dementia due to aftereffects of Parkinson's disease. Preferably, the dementia can be Alzheimer's disease or vascular dementia.

In detail, the pharmaceutical composition comprising flavone-6-C-β-D-glucose derivatives as active ingredients shows remarkable effect in enhancing learning ability, space skills, memory and concentration to a high level in an animal model of memory impairment that is induced by scopolamine or stroke. Thus, it can be useful for preventing or treating cognitive disorders or attention disorders.

Apropos of the present disclosure, the stroke or palsy means a persistence of a rapidly occurred disorder on partial or general brain function by damages to the cranial nerve cells due to cerebrovascular abnormalities over a considerable period.

In detail, the pharmaceutical composition of the present disclosure exhibits remarkable protective effect on cranial nerve cell damage caused by stroke or palsy, thus it can be used for preventing or treating stroke or palsy.

Apropos of the present disclosure, the anxiety disorders mean neuropsychiatric diseases, which interfere with everyday life due to various forms of abnormal and pathological anxiety and fear that transcend the normal emotional reactions. It can be panic disorder, obsessive compulsive disorder or post traumatic stress disorder.

In detail, the pharmaceutical composition of the present disclosure exhibits remarkable effect on anti-anxiety activity, thus it can be used for preventing or treating anxiety disorders.

Apropos of the present disclosure, the sleep disorders mean neuropsychiatric diseases that hinder sleep quantitatively and qualitatively. Specifically, it can be hypersomnia. The hypersomnia means phenomena such as excessive feeling of sleepiness in daytime and struggling to stay awake but fall asleep instantly.

In detail, the pharmaceutical composition of the present disclosure exhibits remarkable awakening effect, thus it can be used for preventing or treating sleep disorders, specifically for hypersomnia.

Additionally, the pharmaceutical composition comprising the flavone-6-C-β-D-glucose derivatives as active ingredients can effectively inhibit memory decline and concentration decline of a dementia-induced mouse by scopolamine or stroke, and anxiety and hypersomnia symptoms of a normal mouse even with a small dose.

Furthermore, the flavone-6-C-β-D-glucose derivatives in the pharmaceutical composition of the present disclosure are ingredients comprised in the above-mentioned herbal extracts, and can effectively treat cognitive disorders, stroke, palsy, attention disorders, anxiety disorders or sleep disorders without side effects.

Therefore, the pharmaceutical composition of the present disclosure can be useful for preventing or treating cognitive disorders, stroke, palsy, attention disorders, anxiety disorders or sleep disorders.

It is preferable for the flavone-6-C-β-D-glucose derivatives of the present disclosure to be included 0.1-50.0 wt % based on total weight of the pharmaceutical composition of the present disclosure, but not limited to the above. The content can vary depending on patient status, disease type and disease progression. Apropos of the pharmaceutical composition of the present disclosure, the flavone-6-C-β-D-glucose derivatives can be administered once or several times at a dose of about 1 mg through 120 mg per a day as for the adults, and preferably, the administration can be once or several times at a dose of about 30 mg through 120 mg. However, the dosage of the compounds can be properly adjusted depending on severity, age, sex, weight and the like of patients, types of drug formulation, and route and duration of administration.

Pharmaceutical Composition Comprising Herbal Extracts

In addition, the present disclosure also provides the pharmaceutical composition for preventing or treating cognitive disorders, stroke, palsy, attention disorders, anxiety disorders or sleep disorders comprising the herbal extracts containing the flavone-6-C-β-D-glucose derivatives as active ingredients.

The flavone-6-C-β-D-glucose derivatives can be selected from the group consisting of swertisin, isovitexin, isoorientin, swertiajaponin and mixtures thereof, and most preferably, it can be swertisin.

Also, the herbal extracts comprising the flavone-6-C-β-D-glucose derivatives can be extracted from *Swertia japonica, Swertia pseudochinensis, Enicostemma hyssopifolium, Swertia mussotii* Franch, *Enicostemma hyssopifolium, Swertia franchetiana, Gentianella austriaca* (Gentianaceae), *Machaerium hirtum* Vell. (Fabaceae), *Aleurites moluccana* L. *Willd.* (Euforbiaceae), *Zizyphus spinosa* (Rhamnaceae), *Belamcanda chinensis* (Iridaceae), *Wilbrandia ebracteata, Cayaponia tayuya* (Cucurbitaceae), *Passiflora incarnata* L. (Passifloraceae), *Commelina communis* L. (Commelinaceae), *Oxalis corniculata* (Oxalidaceae), *Aquilegia oxysepala* Trautv. et Mey (Ranunculoideae), or mixtures thereof.

The *Swertia japonica, Swertia pseudochinensis, Enicostemma hyssopifolium, Swertia mussotii* Franch, *Enicostemma hyssopifolium, Swertia franchetiana, Gentianella austriaca* (Gentianaceae), *Machaerium hirtum* Vell. (Fabaceae), *Aleurites moluccana* L. *Willd.* (Euforbiaceae), *Zizyphus spinosa* (Rhamnaceae), *Belamcanda chinensis* (Iridaceae), *Wilbrandia ebracteata, Cayaponia tayuya* (Cucurbitaceae), *Passiflora incarnata* L. (Passifloraceae), *Commelina communis* L. (Commelinaceae), *Oxalis corniculata* (Oxalidaceae) and *Aquilegia oxysepala* Trautv. et Mey (Ranunculoideae) include swertisin, isovitexin, isoorientin or swertiajaponin among the flavone-6-C-β-D-glucose derivatives represented by Formula 1, thus the pharmaceutical composition comprising the herbal extracts can prevent or treat cognitive disorders, stroke, palsy, attention disorders, anxiety disorders or sleep disorders as swertisin of the flavone-6-C-β-D-glucose derivatives. Furthermore, the same can prevent or treat cognitive disorders, stroke, palsy, attention disorders, anxiety disorders or hypersomnia without side effects because those are herbal extracts.

The pharmaceutical composition of the present disclosure can comprise extract of *Swertia japonica* or *Swertia pseudochinensis*, and preferably, the same can comprise extract of hexane, ethanol or mixtures thereof of a whole plant of *Swertia japonica*.

An extraction solvent for the herbal extracts can be water, alcohol, hexane or mixtures thereof. It is preferable for the alcohol to be $C_1$-$C_4$ lower alcohol, and more preferably to be methanol or ethanol. An extraction method can be shaking extraction, Soxhlet extraction or reflux extraction but not limited to these. It is preferable for extraction temperature to be 40-100° C., and more preferably to be 60-80° C. In addition, it is preferable for extraction duration to be 2-24 hours, and 1-5 times for the extraction time.

The pharmaceutical composition of the present disclosure comprising the herbal extracts as active ingredients can comprise 0.1-50.0 wt % of the herbal extracts based on total weight of the pharmaceutical composition, but not limited to the above. The content can vary depending on patient status, disease type and disease progression.

Apropos of the pharmaceutical composition of the present disclosure comprising the herbal extracts, the herbal extracts can be administered once or several times at a dose of about 10 mg through 1,200 mg per a day as for the adults, and preferably, the administration can be once or several times at a dose of about 300 mg through 1,200 mg. However, the dosage of the compounds can be properly adjusted depending on severity, age, sex, weight and the like of patients, types of drug formulation, and route and duration of administration.

The pharmaceutical composition of the present disclosure comprising the flavone-6-C-β-D-glucose derivatives or the herbal extracts containing the same is safe for a long-term administration for preventing or treating purpose because it has no toxicity and side effects.

The pharmaceutical composition of the present disclosure comprising the flavone-6-C-β-D-glucose derivatives or the herbal extracts containing the same can comprise additives such as pharmaceutically acceptable diluents, binders, disintegrants, lubricants, pH modifiers, antioxidants, solubilizing agents and the like within the scope of the present disclosure.

The diluents can be sugar, starch, microcrystalline cellulose, lactose (lactose hydrate), glucose, D-mannitol, alginate, alkaline earth metal salt, clay, polyethylene glycol, anhydrous calcium hydrogen phosphate or mixtures thereof, and the like.

The binders can be starch, microcrystalline cellulose, highly dispersible silica, mannitol, D-mannitol, sucrose, lactose hydrate, polyethylene glycol, polyvinylpyrrolidone (povidone), polyvinylpyrrolidone copolymers (copovidone), hypromellose, hydroxypropyl cellulose, natural gum, synthetic gum, copovidone, gelatin or mixtures thereof, and the like.

The disintegrants can be starch or modified starch such as sodium starch glycolate, corn starch, potato starch or pregelatinized starch and the like; clay such as bentonite, montmorillonite or veegum and the like; celluloses such as microcrystalline cellulose, hydroxypropyl cellulose or carboxymethyl cellulose and the like; algins such as sodium alginate or alginic acid and the like; cross-linked cellulose such as sodium croscarmellose and the like; gums such as guar gum and xanthan gum and the like; cross-linked polymers such as cross-linked polyvinylpyrrolidone (crospovidone) and the like; effervescent agents such as sodium bicarbonate, citric acid and the like, or mixtures thereof.

The lubricants can be talc, stearic acid, magnesium stearate, calcium stearate, sodium lauryl sulfate, hydrogenated vegetable oil, sodium benzoate, sodium stearyl fumarate, glyceryl behenate, glyceryl monooleate, glyceryl monostearate, glyceryl palm isostearate, colloidal silicon dioxide or mixtures thereof, and the like.

The pH modifiers can be acidifying agents and the like such as acetic acid, adipic acid, ascorbic acid, sodium ascorbate, sodium etherate, malic acid, succinic acid, tartaric acid, fumaric acid and citric acid; and alkalizing agents such as precipitated calcium carbonate, ammonia water, meglumine, sodium carbonate, magnesium oxide, magnesium carbonate, sodium citrate and tribasic calcium phosphate.

The antioxidants can be dibutyl hydroxy toluene, butylated hydroxyanisole, tocopherol acetate, tocopherol, propyl gallate, sodium hydrogen sulfite and sodium pyrosulfite and the like. The solubilizing agents can be polyoxyethylene sorbitan fatty acid esters such as sodium lauryl sulfate and polysorbate and the like, sodium docusate, poloxamer and the like.

The pharmaceutical composition of the present disclosure comprising the flavone-6-C-β-D-glucose derivatives or the herbal extracts containing the same can be formulated as a solid preparation for oral administration. For instance, it can be prepared as tablets, pills, powders, granules, capsules and the like, and these solid preparations can be prepared by mixing the flavone-6-C-β-D-glucose derivatives or the herbal extracts containing the same with at least one excipient such as starch, calcium carbonate, sucrose or lactose, gelatin and the like. Also, lubricants such as magnesium stearate talc can be used together other than simple excipients. Furthermore, the pharmaceutical composition can be formulated as a liquid preparation such as a suspension, liquid for internal use, emulsion, syrup and the like for oral administration. Various excipients such as humectants, sweetening agents, flavoring agents, preservatives and the like other than water and liquid paraffin can be used for formulation of the liquid preparation.

The pharmaceutical composition of the present disclosure comprising the flavone-6-C-β-D-glucose derivatives or the herbal extracts containing the same can comprise sterile aqueous solution, nonaqueous solvent, suspension, emulsion, lyophilized formulation and suppository when formulating for parenteral administration. The nonaqueous solvent and suspension can be vegetable oils such as propylene glycol, polyethylene glycol, olive oil, and injectable esters such as ethyl oleate. A base compound of the suppository can be witepsol, macrogol, Tween 61, cacao butter, laurinum, glycerogelatin and the like.

The term 'administration' used in the present disclosure means introduction of the pharmaceutical composition of the present disclosure for preventing or treating cognitive disorders, stroke, palsy, attention disorders, anxiety disorders or sleep disorders to patients via proper methods, and the route of administration of the pharmaceutical composition of the present disclosure for preventing or treating cognitive disorders, stroke, palsy, attention disorders, anxiety disorders or sleep disorders can be any general routes as long as it reaches to the targeted tissue. The administration route can be oral, intraperitoneal, intravenous, intramuscular, subcutaneous, intranasal, intrapulmonary, intrarectal, intracavitary, intraperitoneal and intrathecal administrations, but not limited to these. For instance, the pharmaceutical composition can be administered through oral, rectal or venous, muscular, subcutaneous, endometrial, or intracerebroventricular injection.

The pharmaceutical composition of the present disclosure comprising the flavone-6-C-β-D-glucose derivatives or the herbal extracts containing the same can be administered once a day or divided into several times at regular intervals.

The pharmaceutical composition of the present disclosure comprising the flavone-6-C-β-D-glucose derivatives or the herbal extracts containing the same can further comprise other active ingredients having effect on treating cognitive disorders, stroke, palsy, attention disorders, anxiety disorders or sleep disorders.

The pharmaceutical composition of the present disclosure comprising the flavone-6-C-β-D-glucose derivatives or the herbal extracts containing the same can be used solely or in combination with various treatment methods such as hormone therapy, drug therapy and the like to prevent or treat cognitive disorders, stroke, palsy, attention disorders, anxiety disorders or sleep disorders.

Food Composition

The present disclosure provides the food composition for preventing or improving cognitive disorders, stroke, palsy, attention disorders, anxiety disorders or sleep disorders comprising the flavone-6-C-β-D-glucose derivatives represented by the above Formula 1 as active ingredients.

Also, the present disclosure provides the food composition for preventing or enhancing cognitive disorders, stroke, palsy, attention disorders, anxiety disorders or sleep disorders comprising the herbal extracts comprising the flavone-6-C-β-D-glucose derivatives as active ingredients.

The food compositions of the present disclosure can be prepared by intactly adding the flavone-6-C-β-D-glucose derivatives, or the herbal extracts containing the same thereto, can comprise additives and the like to other food compositions, functional health foods or beverages.

For instance, the food composition of the present disclosure can comprise sweetening agents such as sucrose, granulated fructose, glucose, D-sorbitol, mannitol, isomaltooligosaccharide, stevioside, aspartame, acesulfame potassium, sucralose, and the like, acidifiers such as anhydrous citric acid, DL-malic acid, succinic acid and its salt, and the like, preservatives such as benzoic acid and its derivative, and the like, various nutritional supplements, vitamins, minerals (electrolyte), flavoring agents such as synthetic and natural flavoring agents, coloring agents, enhancers (cheese, cholate and the like), pectic acid and its salt, alginic acid and its salt, organic acid, protective colloid thickener, pH modifier, stabilizer, preservative, glycerin, alcohol, carbonating agent used for carbonated beverage and the like. Also, the food composition of the present disclosure can comprise pulp for preparation of natural fruit and vegetable juice. The ratio of these additives can be decided within the range of about 20 parts by weight or below per 100 parts by weight of the food composition of the present disclosure.

When the food composition of the present disclosure is prepared as beverages, it can further comprise flavoring agents or natural carbohydrate, which is commonly added to beverages. The natural carbohydrate can be monosaccharide such as glucose and fructose, disaccharide such as maltose and sucrose, polysaccharide such as dextrin and cyclodextrin; or sugar alcohol such as xylitol, sorbitol and erythritol. In addition, the flavoring agent can be natural flavoring agent such as thaumatin, stevia extract (rebaudioside A, glycyrrhizin and the like), or synthetic flavoring agent such as saccharin, aspartame and the like. When the food composition is prepared as beverages, natural carbohydrate can be included as 1-20 g per 100 mL of the composition in general, and preferably 5-12 g per 100 mL of the composition.

The food composition of the present disclosure comprising the flavone-6-C-β-D-glucose derivatives or the herbal extracts containing the same as active ingredients can be prepared as a form of powder, granule, tablet, capsule or beverage, and used as foods, beverage, gum, tea, vitamin complex and health supplement foods.

The food composition of the present disclosure comprising the flavone-6-C-β-D-glucose derivatives or the herbal extracts containing the same as active ingredients can be added to medicaments, foods and beverages to prevent or enhance cognitive disorders, stroke, palsy, attention disorders, anxiety disorders or sleep disorders. For instance, the food composition of the present disclosure can be added to foods, beverages, gums, teas, vitamin complexes, health supplement foods and the like.

The food composition of the present disclosure comprising the flavone-6-C-β-D-glucose derivatives or the herbal extracts containing the same as active ingredients can be added to food or beverage to prevent or enhance cognitive disorders, stroke, palsy, attention disorders, anxiety disorders or sleep disorders. The composition of the present disclosure can be included as 1-5 wt % based on total weight of the food. The same can be included in the ratio of 0.02-10 g in 100 mL of the beverage, and preferably 0.3-1 g.

Method for Preventing or Treating Cognitive Disorders, Stroke, Palsy, Attention Disorders, Anxiety Disorders or Sleep Disorders Moreover, the present disclosure provides the method for preventing, enhancing or treating cognitive disorders, stroke, palsy, attention disorders, anxiety disorders or sleep disorders, comprising administering the pharmaceutical composition or the food composition to subjects in need of the same. Furthermore, the subjects of the present disclosure include mammals, specifically human being.

Pertaining to the present disclosure, the cognitive disorders are directed to neuropsychiatric diseases incurred from functional decline of memory, space skills, concentration, judgment, executive function, linguistic ability and the like. It can be delirium, dementia or amnesia. Also, the dementia can be caused by various causes such as Alzheimer's disease, vascular dementia, attention deficit hyperaction disorder, alcoholic dementia, traumatic dementia and dementia due to the aftereffects of Parkinson's disease. Preferably, the dementia can be Alzheimer's disease or vascular dementia.

Use of the Pharmaceutical Composition and the Food Composition

Also, the present disclosure provides the use of the pharmaceutical composition or the food composition for preparation of a therapeutic agent for preventing, enhancing or treating cognitive disorders, stroke, palsy, attention disorders, anxiety disorders or sleep disorders.

Apropos of the present disclosure, the cognitive disorders are directed to neuropsychiatric diseases incurred from functional decline of memory, space skills, concentration, judgment, executive function, linguistic ability and the like. It can be delirium, dementia or amnesia. Also, the dementia can be caused by various causes such as Alzheimer's disease, vascular dementia, attention deficit hyperaction disorder, alcoholic dementia, traumatic dementia and dementia due to the aftereffects of Parkinson's disease. Preferably, the dementia can be Alzheimer's disease or vascular dementia.

Advantageous Effect

The pharmaceutical composition of the present disclosure comprising the flavone-6-C-β-D-glucose derivatives or the herbal extracts containing the same can effectively prevent or treat cognitive disorders, stroke, palsy, attention disorders, anxiety disorders or sleep disorders.

Also, the food composition of the present disclosure comprising the flavone-6-C-β-D-glucose derivatives or the herbal extracts containing the same as active ingredients can effectively prevent or improve cognitive disorders, stroke, palsy, attention disorders, anxiety disorders or sleep disorders.

BRIEF DESCRIPTION OF DRAWINGS

FIG. 1 illustrates effect of the pharmaceutical composition comprising swertisin, which is one of the flavone-6-C-β-D-glucose derivatives, in enhancing memory and learning abilities as per Alzheimer's disease.

FIG. 2 illustrates effect of the pharmaceutical composition comprising isoorientin, which is one of the flavone-6-C-β-D-glucose derivatives, in enhancing memory and learning abilities as per Alzheimer's disease.

FIG. 3 illustrates effect of the pharmaceutical composition comprising the *Swertia japonica* extract comprising the flavone-6-C-β-D-glucose derivatives in enhancing memory and learning abilities as per Alzheimer's disease.

FIG. 4 illustrates effect of the pharmaceutical composition comprising the *Swertia pseudochinensis* extract comprising the flavone-6-C-β-D-glucose derivatives in enhancing memory and learning abilities as per Alzheimer's disease.

FIGS. 5 and 6 illustrate effect of swertisin, which is one of the flavone-6-C-β-D-glucose derivatives, in enhancing memory and learning abilities as per Alzheimer's disease.

FIGS. 7 and 8 illustrate effect of the pharmaceutical composition comprising the *Swertia japonica* extract comprising the flavone-6-C-β-D-glucose derivatives in enhancing memory and learning abilities as per vascular dementia.

FIG. 9 illustrates effect of the pharmaceutical composition comprising the *Swertia japonica* extract comprising the flavone-6-C-β-D-glucose derivatives in protecting cranial nerve cells as per stroke and palsy.

FIGS. 10 and 11 illustrate effect of swertisin, which is one of the flavone-6-C-β-D-glucose derivatives, in enhancing memory and learning abilities as per vascular dementia.

FIG. 12 illustrates effect of swertisin, which is one of the flavone-6-C-β-D-glucose derivatives, in protecting cranial nerve cells as per stroke and palsy.

FIG. 13 illustrates anti-anxiety effect of swertisin, which is one of the flavone-6-C-β-D-glucose derivatives.

FIG. 14 illustrates awakening effect of swertisin, which is one of the flavone-6-C-β-D-glucose derivatives.

DESCRIPTION OF EMBODIMENTS

The present disclosure will be described more fully hereinafter with reference to the accompanying examples. However, the present disclosure may be embodied in many different forms, and should not be construed as being limited to the embodiments set forth herein.

In addition, reagents and solvents used hereinafter were purchased from Sigma and optical rotatory power was measured by using the JASCO P-1020 polarimeter unless otherwise said. UV was measured by using the Hitachi JP/U3010, IR was measured by using the JASCO FT/IR-5300, NMR was measured by using the Avance 400 (Bruker, 400 MHz) and FAB Mass spectrum was measured by using the JEOL JMS-700 mass spectrometer.

Example 1. Preparation of 70% Ethanol Extract of Swertia japonica Containing Flavone-6-C-β-D-glucose Derivatives Swertia japonica (40 g) was grinded by using a grinder and divided into extraction bottles. 70% ethanol was added to the residue until being higher than the sample surface. The same was extracted twice at 60° C. for 2 hours, and then filtered and concentrated under reduced pressure.

Example 2. Preparation of 70% Ethanol Extract of Swertia pseudochinensis Comprising Flavone-6-C-β-D-glucose Derivatives The extract was prepared in the same manner as Example 1 except that Swertia pseudochinensis (40 g) was used herein instead of Swertia japonica.

Example 3. Separation and Purification of Swertisin and Isoorientin

A column chromatography (Ø 6.5×34.9 cm) was conducted on the 70% ethanol extract of Swertia japonica (10.66 g) prepared in Example 1 with $CH_2Cl_2$-MeOH—$H_2O$ mixed solvent (9:1:0.1→8.5:1.5:0.1→4:1:0.1, v/v, last 100% MeOH) as a mobile phase, and silica gel (70-230 mesh) as a stationary phase. The same was divided into 12 subfractions. MPLC ($C_{18}$ column 130 g, MeOH—$H_2O$ gradient) was conducted on the subfraction 9 (860 mg) to separate compound 1 (100 mg). The fraction 10 (560 mg) was divided into 5 subfractions via Sephadex LH-20 column chromatography (Ø 3.4×38.5 cm) by using a 100% MeOH solvent. MPLC($C_{18}$, 48 g, MeOH—$H_2O$ gradient) was conducted on the subfraction 10-4 (180 g) to further separate the compound 1 (50 mg). The subfraction 12 (4.19 g) was divided into 5 subfractions via Sephadex LH-20 column chromatography (Ø 3.4×33.5 cm) by using a MeOH—$H_2O$ mixed solvent (4:1, v/v). MPLC($C_{18}$, 26 g, MeOH—$H_2O$ gradient) was conducted on the subfraction 12-4 (80 mg) to separate compound 2 (30 g). The structures of the compounds 1 and 2 were identified as swertisin and isoorientin respectively through $^1$H-NMR and $^{13}$C-NMR data analyses, and comparative analysis with the data disclosed in the related document.

[G. Cheng, Y. Bai, Y. Zhao, J. Tao, Y. Liu, G. Tu, L. Ma, N. Liao and X. Xu. Flavonoids from *Ziziphus jujuba* Mill var. *spinosa*. Tetrahedron 2000, 56, 8915-8920.]

[Y. Li, Y. Suo, Z. Liao, L. Ding, The glycosides from *Lomatogonium rotatum*. Natural Product Research 2008, 22-3, 198-202.]

Swertisin: Yellow powder. $^1$H-NMR (400 MHz DMSO-$d_6$), (splitting caused by rotational isomerism): 7.97 (2H, d, J=8.4 Hz, 2', 6'-H); 6.93 (2H, d, J=8.0 Hz, 3', 5'-H); 6.88, 6.86 (1H, s, 8-H); 6.85, 6.84 (1H, s, 3-H), 4.61 (1H, d, J=8.0 Hz, Glc 1"-H), 3.87 (3H, s, $OCH_3$). $^{13}$C-NMR (100 MHz DMSO-$d_6$), (splitting caused by rotational isomerism): Table Isoorientin: Yellow needle. $^1$H-NMR (500 MHz DMSO-$d_6$), (splitting caused by rotational isomerism): 7.43 (1H, d, J=8.5 Hz, 6'-H); 7.41 (1H, s, 2'-H); 6.91 (1H, d, J=8.0 Hz, 5'-H) 6.67 (1H, s, 3-H) 6.48 (1H, s, 8-H), 4.60 (1H, d, J=10.0 Hz, Glc 1"-H). $^{13}$C-NMR (100 MHz DMSO-$d_6$), (splitting caused by rotational isomerism):

TABLE $^{13}$C-NMR Spectral Data for 1 and 2 (in DMSO-$d_6$)

| Position | $\delta_c$ 1 Rotamer 1 | $\delta_c$ 1 Rotamer 2 | 2 |
|---|---|---|---|
| 2 | 163.7 | 163.9 | 163.5 |
| 3 | 103.0 | 103.0 | 102.6 |
| 4 | 181.9 | 182.2 | 181.8 |
| 5 | 159.5 | 160.3 | 156.2 |
| 6 | 109.6 | 109.7 | 108.9 |
| 7 | 164.9 | 164.9 | 163.6 |
| 8 | 90.2 | 91.0 | 93.5 |
| 9 | 156.7 | 156.8 | 160.7 |
| 10 | 104.1 | 104.6 | 103.2 |
| 1' | 120.8 | 120.9 | 118.9 |
| 2' | 128.5 | 128.5 | 113.2 |
| 3, | 116.0 | 116.0 | 145.8 |
| 4' | 161.4 | 161.4 | 149.8 |
| 5' | 116.0 | 116.0 | 76.0 |
| 6' | 128.5 | 128.5 | 121.2 |
| $OCH_3$ | 56.2 | 56.5 | |
| glc 1" | 70.8 | 70.9 | 73.0 |
| 2" | 72.5 | 72.8 | 70.6 |
| 3" | 79.0 | 79.1 | 78.9 |
| 4" | 69.6 | 70.2 | 70.1 |
| 5" | 81.7 | 81.9 | 81.6 |
| 6" | 61.7 | 61.7 | 61.4 |

Experimental Example 1. Observation of Memory-Enhancing Effect in Alzheimer's Disease An experiment was conducted to confirm effects of swertisin or isoorientin, and extracts of *Swertia pseudochinensis* or *Swertia japonica* containing the same prepared in Examples 1 to 3 in treating dementia by using a model of memory impairment induced by scopolamine. Detailed method follows.

1) Preparation of Laboratory Animals

Six-week old ICR mice in about 26 g to 28 g (Orientbio Inc, Republic of Korea) were received water and feed without constraint and adapted for 5 days under an environment having about 23±1° C. of temperature, about 60±10% of humidity and 12-hour light/dark cycle (animal laboratory at College of Pharmacy, Kyung-Hee University), and then used for the experiment.

2) Statistics Process

Every experiment result was processed by using ANOVA (one-way analysis of variance) and a significance test was conducted at a level of $p<0.05$ or below by using Student-Newman-Keuls Test when significance was recognized as exists.

3) Experimental Example 1-1: Passive Avoidance Test 1

An apparatus for measuring passive avoidance reaction was prepared. The apparatus has 2 separated chambers (the first and second chambers) and there is a guillotine-shaped passage that connects the first chamber and the second chamber. The first chamber was maintained brightly by using a light, and the second chamber was maintained darkly. A grid was installed on the floor of the second chamber. The grid generates 0.5 mA of electric shock for 3 seconds when the laboratory animal moved into the dark chamber.

About 30 minutes later, 1 mg/Kg of scopolamine, which was dissolved in distilled water, was intraperitoneally administered to the drug administration groups 1 to 4 and controls 1 and 2 (Ebert, U. et al., Eur. J. Clin. Invest., 28, pp 944-949, 1998), and 0.9% of saline solution was intraperitoneally administered to the control 3. After 30 minutes, passive avoidance learning was conducted on the drug administration groups 1-4 and controls 1-3. In detail, the mice were located in the first chamber (i.e. bright space) and the passage was open after about 20 seconds of observation time, and then latency time of the mice moving to the second chamber (i.e. dark space) was measured. The mice that did not move to the second chamber (i.e. dark space) after 60 seconds from opening of the guillotine-shaped passage were excluded.

Twenty-four hours after the passive avoidance learning, a main experiment was conducted on the drug administration groups 1-4 and controls 1-3. Latency time of the mice of each group moving their 4 legs into the dark space after 10 seconds of observation time from opening of the guillotine-shaped passage was measured up to 300 seconds. It means that the passive avoidance learning and memory are better if the latency time is longer.

The passive avoidance test was conducted on the drug administration groups 1-4 and controls 1-3 in the same manner as the method explained above except that swertisin, which is one of the flavone-6-C-β-D-glucose derivatives prepared in Example 3, was dissolved in 10% Tween 80 and administered to the drug administration groups 1-4 in amounts of 1.25 mg/kg, 2.5 mg/kg, 5 mg/kg and 10 mg/kg respectively.

Average latency time of the mice of each group at the passive avoidance learning and the main experiment were shown in Table 2 and FIG. 1.

TABLE 2

| Group | Passive Avoidance Learning (sec.) | Main Experiment (sec.) |
| --- | --- | --- |
| Drug Admin. Gr. 1 (1.25 mg/kg) | 30.20 ± 14.53 | 67.13 ± 26.08 |
| Drug Admin. Gr. 2 (2.5 mg/kg) | 19.10 ± 10.37 | 82.11 ± 35.20 |

TABLE 2-continued

| Group | Passive Avoidance Learning (sec.) | Main Experiment (sec.) |
| --- | --- | --- |
| Drug Admin. Gr. 3 (5 mg/kg) | 20.40 ± 10.11 | 117.3 ± 44.16 |
| Drug Admin. Gr. 4 (10 mg/kg) | 29.70 ± 18.76 | 117.7 ± 52.28 |
| Control 1 (Donepezil) | 25.60 ± 10.83 | 138.7 ± 34.03 |
| Control 2 | 22.70 ± 14.76 | 35.30 ± 19.04 |
| Control 3 | 30.22 ± 20.24 | 257.7 ± 45.02 |

As shown in Table 2 and FIG. 1, latency time of moving to the second chamber of the drug administration groups 1-4, wherein swertisin prepared in Example 3 was administered, were remarkably extended compared to that of the control 2, wherein scopolamine was administered. In detail, latency time of the drug administration group 1, wherein 1.25 mg/Kg of swertisin was administered, was about 2-fold extended compared to that of the control 2; latency time of the drug administration group 2, wherein 2.5 mg/Kg of swertisin was administered, was about 2.5-fold extended compared to that of the control 2; latency time of the drug administration group 3, wherein 5 mg/Kg of swertisin was administered was about 3-fold extended compared to that of the control 2; and latency time of the drug administration group 4, wherein 10 mg/Kg of swertisin was administered, was about 3-fold extended compared to that of the control 2.

Accordingly, it was confirmed that swertisin prepared in Example 3 was effective for preventing or treating cognitive impairment such as dementia.

4) Experimental Example 1-2: Passive Avoidance Test 2

The passive avoidance test was conducted on the drug administration groups 1-4 and controls 1-3 in the same manner as Experimental Example 1-1 except that isoorientin, which is one of the flavone-6-C-β-D-glucose derivatives prepared in Example 3, was dissolved in 10% Tween 80 and administered to the drug administration groups 1-4 in amounts of 1.25 mg/kg, 2.5 mg/kg, 5 mg/kg and 10 mg/kg respectively.

Average latency time of the mice of each group at the passive avoidance learning and the main experiment were shown in Table 3 and FIG. 2.

TABLE 3

| Group | Passive Avoidance Learning (sec.) | Main Experiment (sec.) |
| --- | --- | --- |
| Drug Admin. Gr. 1 (1.25 mg/kg) | 43.60 ± 5.340 | 41.00 ± 7.988 |
| Drug Admin. Gr. 2 (2.5 mg/kg) | 40.00 ± 5.499 | 80.90 ± 19.44 |
| Drug Admin. Gr. 3 (5 mg/kg) | 35.20 ± 5.236 | 119.3 ± 73.43 |
| Drug Admin. Gr. 4 (10 mg/kg) | 26.80 ± 5.085 | 102.8 ± 15.89 |
| Control 1 (Donepezil) | 21.30 ± 4.964 | 127.8 ± 11.43 |
| Control 2 | 23.00 ± 6.481 | 47.22 ± 5.354 |
| Control 3 | 13.30 ± 3.180 | 265.2 ± 20.12 |

As shown in Table 3 and FIG. 2, latency time of moving to the second chamber of the drug administration groups 1-4, wherein isoorientin prepared in Example 3 was administered, were remarkably extended compared to that of the control 2, wherein scopolamine was administered. In detail, latency time of the drug administration group 2, wherein 2.5 mg/Kg of isoorientin was administered, was about 2-fold extended compared to that of the control 2; latency time of the drug administration group 3, wherein 5 mg/Kg of isoorientin was administered, was about 3-fold extended compared to that of the control 2; and latency time of the drug administration group 4, wherein 10 mg/Kg of isoorientin was administered, was about 2.5-fold extended compared to that of the control 2.

Accordingly, it was confirmed that isoorientin prepared in Example 3 was effective for preventing or treating cognitive impairment such as dementia.

5) Experimental Example 1-3: Passive Avoidance Test 3

The passive avoidance test was conducted on the drug administration groups 1-3 and controls 1-3 in the same manner as Experimental Example 1-1 except that a 70% ethanol extract of *Swertia japonica* prepared in Example 1, was dissolved in 10% Tween and administered to the drug administration groups 1-3 in amounts of 100 mg/kg, 200 mg/kg and 400 mg/kg respectively.

Test result therefrom was shown in Table 4 and FIG. 3.

TABLE 4

| Group | Passive Avoidance Learning | Main Experiment |
| --- | --- | --- |
| Drug Admin. Gr. 1 (100 mg/kg) | 38.20 ± 20.82 | 87.20 ± 70.09 |
| Drug Admin. Gr. 2 (200 mg/kg) | 36.70 ± 14.97 | 136.3 ± 81.70 |
| Drug Admin. Gr. 3 (400 mg/kg) | 38.30 ± 17.93 | 100.4 ± 76.23 |
| Control 1 (Donepezil) | 26.40 ± 16.23 | 169.6 ± 79.98 |
| Control 2 | 31.00 ± 19.28 | 40.90 ± 25.78 |
| Control 3 | 20.78 ± 13.11 | 246.1 ± 56.98 |

As shown in Table 4 and FIG. 3, latency time of moving to the second chamber of the drug administration groups 1-3, wherein the *Swertia japonica* extract containing swertisin prepared in Example 1 was administered, were remarkably extended compared to that of the control 2, wherein scopolamine was administered. In detail, latency time of the drug administration group 1, wherein 100 mg/Kg of the *Swertia japonica* extract containing swertisin was administered, was about 2-fold extended compared to that of the control 2; latency time of the drug administration group 2, wherein 200 mg/Kg of the *Swertia japonica* extract containing swertisin was administered, was about 3-fold extended compared to that of the control 2; and latency time of the drug administration group 3, wherein 400 mg/Kg of the *Swertia japonica* extract containing swertisin was administered, was about 2.5-fold extended compared to that of the control 2.

Accordingly, it was confirmed that the *Swertia japonica* extract containing swertisin prepared in Example 1 was effective for preventing or treating cognitive impairment such as dementia.

6) Experimental Example 1-4: Passive Avoidance Test 4

The passive avoidance test was conducted on the drug administration groups 1-3 and controls 1-3 in the same manner as Experimental Example 1-1 except that a 70% ethanol extract of *Swertia pseudochinensis* prepared in Example 2, was dissolved in 10% Tween 80 and administered to the drug administration groups 1-3 in amounts of 100 mg/kg, 200 mg/kg and 400 mg/kg respectively.

Test result therefrom was shown in Table 5 and FIG. 4.

TABLE 5

| Group | Passive Avoidance Learning | Main Experiment |
| --- | --- | --- |
| Drug Admin. Gr. 1 (100 mg/kg) | 26.50 ± 15.67 | 76.50 ± 37.67 |
| Drug Admin. Gr. 2 (200 mg/kg) | 28.10 ± 8.724 | 111.5 ± 34.24 |
| Drug Admin. Gr. 3 (400 mg/kg) | 26.50 ± 19.78 | 64.00 ± 27.28 |
| Control 1 (Donepezil) | 28.10 ± 19.02 | 159.6 ± 65.51 |
| Control 2 | 29.80 ± 14.18 | 40.44 ± 20.27 |
| Control 3 | 28.20 ± 18.16 | 216.5 ± 64.47 |

As shown in Table 5 and FIG. 4, latency time of moving to the second chamber of the drug administration groups 1-3, wherein the *Swertia pseudochinensis* extract containing swertisin prepared in Example 2 was administered, were remarkably extended compared to that of the control 2, wherein scopolamine was administered. In detail, latency time of the drug administration group 1, wherein 100 mg/Kg of the *Swertia pseudochinensis* extract containing swertisin was administered, was about 2-fold extended compared to that of the control 2; latency time of the drug administration group 2, wherein 200 mg/Kg of the *Swertia pseudochinensis* extract containing swertisin was administered, was about 3-fold extended compared to that of the control 2; and latency time of the drug administration group 3, wherein 400 mg/Kg of the *Swertia pseudochinensis* extract containing swertisin was administered, was about 2-fold extended compared to that of the control 2.

Accordingly, it was confirmed that the *Swertia pseudochinensis* extract containing swertisin prepared in Example 2 was effective for preventing or treating cognitive impairment such as dementia.

7) Experimental Example 5: Y-Maze Test

A Y-maze was prepared for the experiment. The Y-maze has 3 branches and each branch has 42 cm of length, 3 cm of width and 12 cm of height. Angle between any two arms is 120 degrees and the arms were made of black polyvinyl resin.

The mice prepared in the above 1) were separated into 5 groups (10 mice per each group) comprised of drug administration groups 1 and 2, and controls 1 to 3.

The swertisin prepared in Example 3 (8 mg) was dissolved in 4 mL of 10% Tween 80 (Polyoxyethylene sorbitan monooleate: Sigma, U.S.A.), and administered to the drug administration groups 1 and 2 in an amounts of 5 mg/Kg and 10 mg/Kg respectively. Meanwhile, 5 mg/Kg of donepezil was administered to the control 1, and 0.15 mL of 10% Tween 80 was administered to the controls 2 and 3 respectively.

About 30 minutes later, 1 mg/Kg of scopolamine, which was dissolved in distilled water, was intraperitoneally administered to the drug administration groups 1 and 2, and controls 1 and 2 (Ebert, U. et al., Eur. J. Clin. Invest., 28, pp. 944-949, 1998), and 0.9% of saline solution was intraperitoneally administered to the control 3.

After 30 minutes, mice of the drug administration groups 1 and 2, and the controls 1-3 were carefully located on each branches of the Y-maze, which was divided as A, B and C respectively, and let the mice move freely for 8 minutes, and then recorded branches where mice have entered. The entrance was recorded when the entire body (i.e. including the tail) has completely entered. It was also recorded when the mice entered again into the branch that the mice have entered before.

One point was scored when the mouse sequentially entered into 3 different branches (actual alternation). Alternation behavior is defined as sequentially entering into every 3 branch, and it was converted into % via Equation 1 below (Sarter, M. et al., Psychopharmacology., 94, pp. 491-495, 1998).

$$\text{Alternation Behavior (\%)} = \frac{\text{Actual Alternation}}{\text{Maximum Alternation}} \times 100 \quad \text{[Equation 1]}$$

(Maximum Alternation: Total Entrance − 2)

Alternation behavior converted by Equation 1 was shown in Table 6 and FIG. 5, and the total entry, which means total number of entry to each branch, was shown in Table 7 and FIG. 6.

TABLE 6

| Group | Alternation Behavior (%) |
| --- | --- |
| Drug Admin. Gr. 1 (5 mg/kg) | 56.22 ± 12.29 |
| Drug Admin. Gr. 2 (10 mg/kg) | 59.36 ± 5.653 |
| Control 1 (Donepezil) | 61.49 ± 5.447 |
| Control 2 | 46.93 ± 10.41 |
| Control 3 | 75.32 ± 6.167 |

TABLE 7

| Group | Total Entry |
| --- | --- |
| Drug Admin. Gr. 1 (5 mg/kg) | 27.10 ± 7.795 |
| Drug Admin. Gr. 2 (10 mg/kg) | 28.88 ± 4.155 |
| Control 1 (Donepezil) | 29.30 ± 4.296 |
| Control 2 | 33.11 ± 3.822 |
| Control 3 | 27.30 ± 3.335 |

As shown in Table 6 and FIG. 5, alternation behavior of the drug administration groups 1 and 2, wherein swertisin prepared in Example 3 was administered, was increased compared to that of the control 2, wherein scopolamine was administered, and specifically, the drug administration group 2 exhibited similar level of alternation behavior to that of the control 1, wherein donepezil was administered.

Also, as shown in Table 7 and FIG. 6, the total entry of the drug administration groups 1 and 2, and the controls 1-3 were shown as having a similar value. Therefore, it can be known that change of mouse activity was irrelevant to increase of the alternation behavior. Thus, it was confirmed that learning, memory and attention abilities of the mice of the drug administration groups 1 and 2 were remarkably improved by swertisin.

Accordingly, it was confirmed that swertisin, which is one of the flavone-6-C-β-D-glucose derivatives prepared in Example 2 was effective in preventing or treating cognitive impairment such as Alzheimer's disease, and attention disorders.

Experimental Example 2: Observation of Enhancing Effect on Memory in Vascular Dementia and Protective Effect on Cranial Nerve Cells in Stroke and Palsy 1) Preparation of Laboratory Animals Seven-week old ICR mice in about 30 g to 35 g (Orientbio Inc, Republic of Korea) were received water and feed without constraint and adapted for 5 days under an environment having about 23±1° C. of temperature, about 60±10% of humidity and 12-hour light/dark cycle (animal laboratory at College of Pharmacy, Kyung-Hee University), and then used for the experiment.

2) Statistics Process

Every experiment result was processed by using ANOVA (one-way analysis of variance) and a significance test was conducted at a level of $p<0.05$ or below by using Student-Newman-Keuls Test when significance was recognized as exists.

3) Preparation of Mouse Model of Stroke

The laboratory animal in 1) was located in an operating room, adapted for 60 minutes, and anesthetized in a space providing anaesthetic gasses (nitrous oxide: 70%; oxygen: 30%; isoflurane: 2.0%). Pain reflex was examined to confirm the anesthesia. The laboratory animal was lain down straight on an operating table, and fixed its upper limb and head. Skin from the spot, where the upper limb and the center line meet, was incised as 1.5 cm to expose the both common carotid arteries by using tweezers while not damaging the tissues. Tissues and nerves attached to the exposed carotid arteries were separated and fixed with an aneurysm clip. The clip was removed after 15 minutes and reperfused, and the incised area was sutured with sutures. After the suture, the laboratory animal was immediately moved to a recovery room (32-33° C., $O_2$ enrichment condition) and kept until it recovers from anesthesia. Observation on its weight and status was conducted once a day for 4 days after the operation.

4) Experimental Example 2-1: Y-Maze Test

Administration of the *Swertia japonica* extract prepared in Example 1 was initiated to the mice prepared in the 1) immediately after the operation 3), and kept administering at the same time for 7 days. Five groups (5 mice per each group) were prepared as drug administration groups 1, 2 and 3, wherein the *Swertia japonica* extract prepared in Example 1 was administered thereto; and controls 1 and 2. 50 mg/kg, 100 mg/kg and 200 mg/kg of the *Swertia japonica* extract was administered to the drug administration groups 1, 2 and 3 respectively; and 0.15 mL of Tween 80 was administered to the controls 1 and 2 respectively. At the 7th day from the initial administration, the Y-maze test was conducted for the drug administration groups 1 to 3 and the controls 1 to 2 in the same manner as Experimental Example 1-5.

After 60 minutes, mice of the drug administration groups 1-3 and the controls 1-2 were carefully located on each branches of the Y-maze, which was divided as A, B and C respectively, and let the mice move freely for 8 minutes, and then recorded branches that mice have entered. The entrance was recorded when the entire body (i.e. including the tail) has completely entered. It was also recorded when the mice entered again into the branch that the mice have entered before. The result was converted into % via Equation 1.

Alternation behavior converted by Equation 1 was shown in FIG. 7 and Table 8, and the total entry, which means total number of entry to each branch, was shown in FIG. 8 and Table 9.

TABLE 8

| Group | Alternation Behavior (%) |
| --- | --- |
| Drug Admin. Gr. 1 (50 mg/kg) | 53.16 ± 11.36 |
| Drug Admin. Gr. 2 (100 mg/kg) | 66.28 ± 9.827 |
| Drug Admin. Gr. 3 (200 mg/kg) | 70.53 ± 12.11 |
| Control 1 (Stroke-induced Group) | 46.62 ± 10.01 |
| Control 2 | 77.96 ± 17.95 |

TABLE 9

| Group | Total Entry |
| --- | --- |
| Drug Admin. Gr. 1 (50 mg/kg) | 23.40 ± 4.450 |
| Drug Admin. Gr. 2 (100 mg/kg) | 20.50 ± 8.888 |
| Drug Admin. Gr. 3 (200 mg/kg) | 23.00 ± 3.162 |
| Control 1 (Stroke-induced Group) | 20.00 ± 5.050 |
| Control 2 | 24.20 ± 2.168 |

As shown in Table 8 and FIG. 7, alternation behavior of the drug administration groups 1-3, wherein the *Swertia japonica* extract prepared in Example 1 was administered, was increased compared to that of the control 1, wherein stroke was induced, and the drug administration group 3 exhibited similar level of alternation behavior to the control 2, which is a normal group.

Also, as shown in Table 9 and FIG. 8, the total entry of the drug administration groups 1-3, and the controls 1-2 were shown as having a similar value. Therefore, it can be known that change of mouse activity was irrelevant to increase of the alternation behavior. Thus, it was confirmed that learning and memory abilities of the mice of the drug administration groups 1-3 were remarkably improved by the *Swertia japonica* extract.

Meanwhile, upon termination of the Y-maze test, a 4% paraformaldehyde fixation was conducted on the drug administration groups 1-3 and the control 2, and brain was excised. Paraformaldehyde-fixed brain sample was washed and section having 30 μm of thickness was prepared therefrom. The Nissl staining, which can stain a native region of brain cells in normal status, was performed. Brain cell damage in the hippocampal region of the drug administration groups 1-3, wherein the *Swertia japonica* extract prepared in Example 1 was administered, and the controls 1 and 2 was assessed through a neurological scoring. Pertaining to the evaluation standard, 0 point was scored when there was no damage on the hippocampal region; 1 point for 0-30% of damage; 2 points for 30-60% of damage; and 3 points for 60-100% of damage. The points were scored by 3 people who have no knowledge of the drug administration groups and the controls. Average point was used to calculate the degree of damage. The neurological score according to the evaluation standard was shown in FIG. 9 and Table 10.

TABLE 10

| Group | Neurological Score |
| --- | --- |
| Drug Admin. Gr. 1 (50 mg/kg) | 1.9170 ± 0.8333 |
| Drug Admin. Gr. 2 (100 mg/kg) | 1.6670 ± 0.8165 |
| Drug Admin. Gr. 3 (200 mg/kg) | 0.8889 ± 0.1925 |
| Drug Admin. Gr. 1 (Stroke-induced Group) | 2.3330 ± 0.4714 |
| Control 2 | 0.0000 ± 0.0000 |

As shown in Table 10 and FIG. 9, the neurological score of the drug administration groups 1-3, wherein the *Swertia japonica* extract prepared in Example 1 was administered, was decreased compared to that of the control 1, wherein stroke was induced, and specifically, the drug administration group 3 exhibited significant result to the stroke-induced group. When considering that the neurological score reflects the damaged brain cells of the hippocampal region in the brain, it was confirmed that the damaged brain cells of the mouse model of stroke in drug administration groups 1-3 were remarkably protected by the *Swertia japonica* extract.

5) Experimental Example 2-2: Y-Maze Test

Administration of swertisin prepared in Example 3 was initiated to the mice prepared in 1) immediately after the operation 3), and kept administering at the same time for 7 days. Five groups (5 mice per each group) were prepared as drug administration groups 1, 2 and 3, wherein swertisin prepared in Example 3 was administered thereto; and controls 1 and 2. 50 mg/kg, 100 mg/kg and 200 mg/kg of swertisin was administered to the drug administration groups 1, 2 and 3 respectively; and 0.15 mL of Tween 80 was administered to the controls 1 and 2 respectively. At the 7th day from the initial administration, the Y-maze test was conducted for the drug administration groups 1 to 3 and the controls 1 to 2 in the same manner as Experimental Example 1.

After 60 minutes, mice of the drug administration groups 1-3 and the controls 1-2 were carefully located on each branches of the Y-maze, which was divided as A, B and C respectively, and let the mice move freely for 8 minutes, and then recorded branches that mice have entered. The entrance was recorded when the entire body (i.e. including the tail) has completely entered. It was also recorded when the mice entered again into the branch that the mice have entered before. The result was converted into % via Equation 1.

Alternation behavior converted by Equation 1 was shown in FIG. 10 and Table 11, and the total entry, which means total number of entry to each branch, was shown in FIG. 11 and Table 12.

TABLE 11

| Group | Alternation Behavior (%) |
| --- | --- |
| Drug Admin. Gr. 1 (50 mg/kg) | 56.10 ± 7.431 |
| Drug Admin. Gr. 2 (100 mg/kg) | 57.58 ± 12.86 |
| Drug Admin. Gr. 3 (200 mg/kg) | 70.46 ± 15.74 |
| Control 1(Stroke-induced Group) | 51.84 ± 11.00 |
| Control 2 | 77.69 ± 4.804 |

TABLE 12

| Group | Total Entry |
| --- | --- |
| Drug Admin. Gr. 1 (50 mg/kg) | 24.14 ± 2.478 |
| Drug Admin. Gr. 2 (100 mg/kg) | 28.50 ± 6.364 |
| Drug Admin. Gr. 3 (200 mg/kg) | 22.00 ± 5.958 |
| Control 1(Stroke-induced Group) | 23.33 ± 3.445 |
| Control 2 | 25.20 ± 6.017 |

As shown in Table 11 and FIG. 10, alternation behavior of the drug administration groups 1-3, wherein swertisin prepared in Example 3 was administered, was increased compared to that of the control 2, wherein stroke was induced, and specifically, the drug administration group 3 exhibited similar level of alternation behavior to the control 2, which is a normal group.

Also, as shown in Table 12 and FIG. 11, the total entry of the drug administration groups 1-3, and the controls 1-2 were shown as having a similar value. Therefore, it can be known that change of mouse activity was irrelevant to increase of the alternation behavior. Thus, it was confirmed that learning and memory abilities of the mouse model of stroke in the drug administration groups 1-3 were remarkably improved by swertisin.

Upon termination of the Y-maze test, the drug administration groups 1-3 and the control 2 were sacrificed to prepare the brain section, and the Nissl staining was conducted to evaluate brain cell damage in the hippocampal region of the drug administration groups 1-3, wherein swertisin prepared in Example 3 was administered, and the controls 1 and 2 through the neurological scoring. The neurological score according to the evaluation standard was shown in FIG. 12 and Table 13.

TABLE 13

| Group | Neurological Score |
| --- | --- |
| Drug Admin. Gr. 1(50 mg/kg) | 1.8130 ± 0.3750 |
| Drug Admin. Gr. 2(100 mg/kg) | 1.2500 ± 0.2500 |
| Drug Admin. Gr. 3(200 mg/kg) | 1.1670 ± 0.5204 |
| Control 1(Stroke-induced Group) | 2.5630 ± 0.2577 |
| Control 2 | 0.0000 ± 0.0000 |

As shown in Table 13 and FIG. 12, the neurological score of the drug administration groups 1-3, wherein swertisin prepared in Example 3 was administered, was decreased compared to that of the control 1, wherein stroke was induced, and specifically, the drug administration group 3 exhibited significant result to the stroke-induced group. When considering that the neurological score reflects the damaged brain cells of the hippocampal region in the brain, it was confirmed that the damaged brain cells of the mouse model of stroke in drug administration groups 1-3 were remarkably protected by swertisin.

Experimental Example 3: Observation of Alleviating Effect in Anxiety Symptoms

1) Preparation of Laboratory Animals

Six-week old ICR mice in about 26 g to 28 g (Orientbio Inc, Republic of Korea) were received water and feed without constraint and adapted for 5 days under an environment having about 23±1° C. of temperature, about 60±10% of humidity and 12-hour light/dark cycle (animal laboratory at College of Pharmacy, Kyung-Hee University), and then used for the experiment.

2) Statistics Process

Every experiment result was processed by using ANOVA (one-way analysis of variance) and a significance test was conducted at a level of p<0.05 or below by using Student-Newman-Keuls Test when significance was recognized as exists.

3) Experimental Example 3-1: Marble Burying Test

As a method of measuring alleviation of anxiety symptoms in a normal status, the marble burying test was conducted based on the nature of mice that they dig when feel anxiety. Inside of a cage in size of 40 cm s 27 cm s 18 cm was covered with straw to the height of 4 cm, and 25 marbles having same pattern were arranged at intervals of 3 cm. Two groups (10 mice per each group) were prepared as the drug administration group 1, wherein swertisin, which is one of the flavone-6-C-β-D-glucose derivatives prepared in Example 3, was administered, and the control 1. Swertisin (10 mg/kg) was administered to the drug administration group 1, and 0.15 mL of 10% Tween 80 was administered to the control 1.

After 60 minutes of administration, mice of the drug administration group 1 and the control 1 were carefully located in the cage having the marbles and the mice were allowed to move freely for 30 minutes. After 30 minutes, the number of buried marbles under straw was counted. At this time, 1 point was given when the marble was completely buried and invisible; and 0.5 point was given when only half of the marble was buried. The more the number of buried marbles, it was assessed that the laboratory animal feels anxiety severer (Broekkamp, C L. et al., Eur J Pharmacol., 126, pp 223-229, 1986).

Result of the test is shown in Table 14 and FIG. 13.

TABLE 14

| Group | Number of Buried Marbles |
| --- | --- |
| Drug Admin. Gr. 1 (10 mg/kg) | 21.78 ± 1.856 |
| Control 1 | 18.78 ± 3.563 |

As shown in Table 14 and FIG. 13, the number of the buried marbles in the drug administration group 1, wherein swertisin prepared in Example 3 was administered, was decreased compared to that of the control 1. Therefore, it was confirmed that the anxiety symptoms that the control 1 in a normal status feels were remarkably decreased by swertisin of the drug administration group 1.

Experimental Example 4: Observation of Awakening Effect in Hypersomnia Symptoms

1) Preparation of Laboratory Animals

Six-week old ICR mice in about 26 g to 28 g (Orientbio Inc, Republic of Korea) were received water and feed without constraint and adapted for 5 days under an environment having about 23±1° C. of temperature, about 60±10% of humidity and 12-hour light/dark cycle (animal laboratory at College of Pharmacy, Kyung-Hee University), and then used for the experiment. Foods were blocked at 24 hours before the test.

2) Statistics Process

Every experiment result was processed by using ANOVA (one-way analysis of variance) and a significance test was conducted at a level of p<0.05 or below by using Student-Newman-Keuls Test when significance was recognized as exists.

3) Experimental Example 4-1: Sleep-Inducing Test

The mice prepared in 1) were divided into 2 groups (10 mice per each group) including the drug administration group 1, wherein swertisin was administered, and the controls 1 and 2. Swertisin prepared in Example 3 was dissolved in 10% Tween 80 (Polyoxyethylene sorbitan monooleate: Sigma, U.S.A.) and administered to the drug administration group 1 in an amount of 10 mg/kg. Meanwhile, 0.15 mL of 10% Tween 80 was administered to the control 1.

After 1 hour of administration, pentobarbital was dissolved in a saline solution and intraperitoneally administered to the mouse in an amount of 60 mg/kg. The mouse was located in the cage. At this time, straw was laid in the cage only enough to cover the floor, and only one mouse was located in the cage for observation. When there was no righting reflex (i.e. a reflex that corrects the orientation of the body when the mouse is taken out of its normal upright position) after administration of pentobarbital, the time taken after the administration was regarded as the time taken for sleep induction. When the mouse showed righting reflex and corrected its orientation of the body thereafter, the mouse was deemed as awaken and sleep duration was calculated.

Result of the test is shown in Table 15 and FIG. 14 below.

TABLE 15

| Group | Total Sleep Time (min.) |
|---|---|
| Drug Admin. Gr. 1 (10 mg/kg) | 94.47 ± 21.83 |
| Control 1 | 122.6 ± 7.348 |

As shown in Table 15 and FIG. 14, total sleep time of the drug administration group 1, wherein swertisin was administered, was remarkably decreased compared to the control 1. Therefore, it was observed that administration of swertisin, which is one of the flavone-6-C-β-D-glucose derivatives, showed an awakening effect in normal status.

Preparation of Formulation and Food Composition

Preparation of Powders

The Swertia japonica extract or the Swertia pseudochinensis extract comprising swertisin prepared in Example 1 or 2 (20 mg), lactose (100 mg) and talc (10 mg) were mixed. A sealed pouch was filled with the same to prepare the powders.

Preparation of Tablets

Tablets were prepared by using the Swertia japonica extract or the Swertia pseudochinensis extract comprising swertisin prepared in Example 1 or 2 and ingredients listed in Table 16.

TABLE 16

| Ingredient | Content (mg) |
|---|---|
| Swertia japonica extract or Swertia pseudochinensis extract (Example 1 or 2) | 10 |
| Corn Starch | 100 |
| Lactose | 100 |
| Magnesium Stearate | 2 |

The above ingredients were mixed and compressed according to conventional tablet manufacturing methods to prepare the tablets.

Preparation of Capsules

Capsules were prepared by using the Swertia japonica extract or the Swertia pseudochinensis extract comprising swertisin prepared in Example 1 or 2 and ingredients listed in Table 17.

TABLE 17

| Ingredient | Content (mg) |
|---|---|
| Swertia japonica extract or Swertia pseudochinensis extract (Example 1 or 2) | 10 |

TABLE 17-continued

| Ingredient | Content (mg) |
|---|---|
| Crystalline Cellulose | 100 |
| Lactose | 100 |
| Magnesium Stearate | 2 |

The above ingredients were mixed and a gelatin capsule was filled with the same according to conventional capsule manufacturing methods to prepare the capsules.

Preparation of Injections

Injections were prepared by using the Swertia japonica extract or the Swertia pseudochinensis extract comprising swertisin prepared in Example 1 or 2 and ingredients listed in Table 18.

TABLE 18

| Ingredient | Content (mg) |
|---|---|
| Swertia japonica extract or Swertia pseudochinensis extract (Example 1 or 2) | 10 |
| Mannitol | 180 |
| Sterile Distilled Water for Injection | 2974 |
| $Na_2HPO_4, 12H_2O$ | 26 |

A solution was prepared by mixing the above ingredients according to the conventional methods. A 2 ml ample was filled with the solution. The same was sterilized to prepare the injections.

Preparation of Liquid Solutions

Liquid solutions were prepared by using the Swertia japonica extract or the Swertia pseudochinensis extract comprising swertisin prepared in Example 1 or 2 and ingredients listed in Table 19.

TABLE 19

| Ingredient | Content |
|---|---|
| Swertia japonica extract or Swertia pseudochinensis extract (Example 1 or 2) | 20 mg |
| Isomerose | 10 g |
| Mannitol | 5 g |
| Purified Water | 85 ml |

A solution (100 ml) was prepared by adding and dissolving each ingredient listed in Table 19 to purified water. Lemon scent was added thereto. Purified water was added thereto again. A brown bottle was filled with the solution. The same was sterilized to prepare the liquid solutions.

Preparation of Health Food Composition

The health food composition was prepared by using the Swertia japonica extract or the Swertia pseudochinensis extract comprising swertisin prepared in Example 1 or 2 and ingredients listed in Table 20.

TABLE 20

| Ingredient | Content |
|---|---|
| Swertia japonica extract or Swertia pseudochinensis extract (Example 1 or 2) | 1000 mg |
| Nicotinic Acid Amide | 1.7 mg |
| Folate | 50 μg |
| Calcium Pantothenate | 0.5 mg |

TABLE 20-continued

| Ingredient | Content |
| --- | --- |
| Ferrous Sulfate | 1.75 mg |
| Zinc Oxide | 0.82 mg |
| Magnesium Carbonate | 25.3 mg |
| Monopotassium Phosphate | 15 mg |
| Dicalcium Phosphate | 55 mg |
| Potassium Citrate | 90 mg |
| Calcium Carbonate | 100 mg |
| Vitamin Complex | q.s |
| Mineral Complex | q.s |

The above ingredients were mixed according to the conventional health food manufacturing methods, and granules were prepared to prepare the health food composition according to the conventional methods.

Preparation of Health Beverage

The health beverage was prepared by using the *Swertia japonica* extract or the *Swertia pseudochinensis* extract comprising swertisin prepared in Example 1 or 2 and ingredients listed in Table 21.

TABLE 21

| Ingredient | Content |
| --- | --- |
| *Swertia japonica* extract or *Swertia pseudochinensis* extract (Example 1 or 2) | 1000 mg |
| Citric Acid | 1000 mg |
| Oligosaccharides | 10 0 g |
| Plum Concentrate | 2 g |
| Taurine | 1 g |
| Purified Water | 900 mL in total |

The ingredients listed in Table 21 were dissolved in purified water according to the conventional health beverage manufacturing methods to prepare a solution (900 ml). The solution was stir heated at 85° C. for 1 hour. The solution was then filtered and obtained in a 2 l container. The same was seal sterilized and kept refrigerated to prepare the health beverage.

INDUSTRIAL APPLICABILITY

The composition of the present disclosure comprising flavone-6-C-β-D-glucose derivatives as active ingredients can prevent, improve or treat cognitive disorders, stroke, palsy, attention disorders, anxiety disorders or sleep disorders.

The invention claimed is:

1. A method for treating cognitive disorders, stroke, palsy, attention disorders, anxiety disorders or sleep disorders, comprising administering a pharmaceutical composition comprising a purified swertisin to a subject in need thereof.

2. The method of claim 1, wherein the swertisin is administered with at least one herbal extract selected from a group consisting of *Swertia japonica, Swertia pseudochinensis, Enicostemma hyssopifolium, Swertia mussotii* Franch., *Enicostemma hyssopifolium, Swertia franchetiana, Gentianella austriaca* (Gentianaceae), *Machaerium hirtum* Vell. (Fabaceae), *Aleurites moluccana* L. *Willd.* (Euforbiaceae), *Zizyphus spinosa* (Rhamnaceae), *Belamcanda chinensis* (Iridaceae), *Wilbrandia ebracteata, Cayaponia tayuya* (Cucurbitaceae), *Commelina communis* L. (Commelinaceae) and *Aquilegia oxysepala* Trautv. et Mey (Ranunculoideae).

3. The method of claim 1, wherein the cognitive disorder is due to stroke, palsy, delirium, dementia or amnesia.

4. The method of claim 3, wherein the dementia is Alzheimer's disease, vascular dementia, dementia caused by attention deficit hyperaction disorder, alcoholic dementia, traumatic dementia and dementia due to aftereffects of Parkinson's disease.

5. The method of claim 3, wherein the dementia is Alzheimer's disease or vascular dementia.

6. The method of claim 3, wherein the stroke or palsy is dementia caused by cerebral infarction or cerebral ischemia.

7. The method of claim 1, wherein the stroke or palsy is a cranial nerve cell damage caused by cerebral infarction or cerebral ischemia.

8. The method of claim 1, wherein the anxiety disorder is panic disorder, obsessive compulsive disorder or post-traumatic stress disorder.

9. The method of claim 1, wherein the sleep disorder is hypersomnia.

10. A method for treating cognitive disorders, stroke, palsy, attention disorders, anxiety disorders or sleep disorders, comprising administering a food composition comprising a purified swertisin to a subject in need thereof.

11. The method of claim 10, wherein the swertisin is administered with at least one extract of an herbal drug selected from the group consisting of *Swertia japonica, Swertia pseudochinensis, Enicostemma hyssopifolium, Swertia mussotii* Franch., *Enicostemma hyssopifolium, Swertia franchetiana, Gentianella austriaca* (Gentianaceae), *Machaerium hirtum* Vell. (Fabaceae), *Aleurites moluccana* L. *Willd.* (Euforbiaceae), *Zizyphus spinosa* (Rhamnaceae), *Belamcanda chinensis* (Iridaceae), *Wilbrandia ebracteata, Cayaponia tayuya* (Cucurbitaceae), *Commelina communis* L. (Commelinaceae) and *Aquilegia oxysepala* Trautv. et Mey (Ranunculoideae).

12. A method for treating a cognitive disorder, stroke, palsy or an attention disorder, comprising administering a pharmaceutical composition comprising a purified isoorientin to a subject in need thereof.

13. A method for treating cognitive disorders, stroke, palsy or attention disorders, comprising administering a food composition comprising a purified isoorientin to a subject in need thereof.

\* \* \* \* \*